US010322174B2

(12) United States Patent
Bilsborough et al.

(10) Patent No.: US 10,322,174 B2
(45) Date of Patent: Jun. 18, 2019

(54) NEUTRALIZING ANTI-TL1A MONOCLONAL ANTIBODIES

(71) Applicant: Cedars-Sinai Medical Center, Los Angeles, CA (US)

(72) Inventors: Janine Bilsborough, Simi Valley, CA (US); Stephan Targan, Santa Monica, CA (US); Bradley Henkle, West Hollywood, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 15/792,266

(22) Filed: Oct. 24, 2017

(65) Prior Publication Data

US 2018/0110855 A1 Apr. 26, 2018

Related U.S. Application Data

(60) Provisional application No. 62/413,188, filed on Oct. 26, 2016.

(51) Int. Cl.
*C07K 16/24* (2006.01)
*A61K 39/395* (2006.01)
*A61P 37/00* (2006.01)
*A61P 1/02* (2006.01)
*A61P 29/00* (2006.01)
*A61K 48/00* (2006.01)
*C07K 16/28* (2006.01)
*C07K 14/525* (2006.01)
*A61K 39/00* (2006.01)

(52) U.S. Cl.
CPC ...... *A61K 39/39533* (2013.01); *A61K 48/005* (2013.01); *A61P 1/02* (2018.01); *A61P 29/00* (2018.01); *A61P 37/00* (2018.01); *C07K 16/241* (2013.01); *C07K 16/2809* (2013.01); *A61K 39/3955* (2013.01); *A61K 2039/505* (2013.01); *C07K 2317/24* (2013.01); *C07K 2317/56* (2013.01); *C07K 2317/565* (2013.01); *C07K 2317/76* (2013.01); *C07K 2317/90* (2013.01)

(58) Field of Classification Search
CPC .......... A61K 2039/505; A61K 39/3955; A61K 31/395; C07K 2317/565; C07K 2317/24; C07K 2317/56; C07K 16/00; C07K 16/241

See application file for complete search history.

(56) References Cited

U.S. PATENT DOCUMENTS

| | | |
|---|---|---|
| 4,518,584 A | 5/1985 | Mark et al. |
| 4,737,462 A | 4/1988 | Mark et al. |
| 4,946,778 A | 8/1990 | Ladner et al. |
| 5,225,539 A | 7/1993 | Winter |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,861,155 A | 1/1999 | Lin |
| 5,885,793 A | 3/1999 | Griffiths et al. |
| 5,969,108 A | 10/1999 | McCafferty et al. |
| 6,172,197 B1 | 1/2001 | McCafferty et al. |
| 6,297,367 B1 | 10/2001 | Tribouley |
| 6,300,064 B1 | 10/2001 | Knappik et al. |
| 6,407,213 B1 | 6/2002 | Carter et al. |
| 6,479,284 B1 | 11/2002 | Marasco et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,599,719 B2 | 7/2003 | Yu et al. |
| 6,632,976 B1 | 10/2003 | Tomizuka et al. |
| 6,653,068 B2 | 11/2003 | Frisch et al. |
| 6,706,484 B1 | 3/2004 | Knappik et al. |
| 6,824,767 B2 | 11/2004 | Yu et al. |
| 6,824,989 B1 | 11/2004 | Eisinger et al. |
| 6,835,823 B2 | 12/2004 | Le et al. |
| 7,264,963 B1 | 9/2007 | Knappik et al. |
| 7,597,886 B2 | 10/2009 | Yu et al. |
| 7,612,181 B2 | 11/2009 | Wu et al. |

(Continued)

FOREIGN PATENT DOCUMENTS

| | | |
|---|---|---|
| EP | 2462165 B1 | 5/2016 |
| EP | 2638069 B1 | 1/2018 |

(Continued)

OTHER PUBLICATIONS

Aiba et al. The role of TL1A and DR3 in autoimmune and inflammatory diseases. Mediators Inflamm vol. 2013: 258164, 2013; 9 total pages.*
Migone et al. TL1A is a TNF-like ligand for DR3 and TR6/DcR3 and functions as a T cell costimulator. Immunity 16: 479-492, 2002.*
R&D datasheet for human/mouse TL1A/TNFSF15 antibody, catalog No. MAB7441; clone #293327; Feb. 7, 2018.*
Reichwald et al. TL1A induces TCR independent IL-6 and TNF-alpha production and growth of PLZF leukocytes. PLOS ONE 9(1): e85793, 2013.*
Richard et al. The TNF-family cytokine TL1A: from lymphocyte costimulator to disease co-conspirator. J Leukocyte Biol 98: 333-345, 2015.*

(Continued)

*Primary Examiner* — Bridget E Bunner
(74) *Attorney, Agent, or Firm* — Wilson Sonsini Goodrich & Rosati

(57) ABSTRACT

Described herein are methods and pharmaceutical compositions for the treatment of inflammatory bowel disease (IBD), Crohn's Disease (CD), ulcerative colitis (UC) and medically refractive-ulcerative colitis (MR-UC). In particular, disclosed are anti-TL1A antibodies useful for the treatment of IBD.

7 Claims, 4 Drawing Sheets

Specification includes a Sequence Listing.

(56) References Cited

U.S. PATENT DOCUMENTS

| | | |
|---|---|---|
| 7,708,996 B2 | 5/2010 | Yu et al. |
| 7,820,798 B2 | 10/2010 | Yu et al. |
| 8,003,099 B2 | 8/2011 | Auer et al. |
| 8,017,122 B2 | 9/2011 | Siadak et al. |
| 8,093,363 B2 | 1/2012 | Yu et al. |
| 8,263,743 B2 | 9/2012 | Smith et al. |
| 8,409,577 B2 | 4/2013 | Thompson et al. |
| 8,524,869 B2 | 9/2013 | Smith et al. |
| 8,642,741 B2 | 2/2014 | Classon et al. |
| 8,728,282 B2 | 5/2014 | Niu |
| 8,728,475 B2 | 5/2014 | Burkly et al. |
| 8,728,482 B2 | 5/2014 | Smith et al. |
| 8,859,739 B2 | 10/2014 | Kontermann et al. |
| 8,883,975 B2 | 11/2014 | Brandt et al. |
| 9,017,679 B2 | 4/2015 | Podack et al. |
| 9,068,003 B2 | 6/2015 | Siegel et al. |
| 9,102,733 B2 | 8/2015 | Endl et al. |
| 9,290,576 B2 | 3/2016 | Attinger et al. |
| 9,416,185 B2 | 8/2016 | Smith et al. |
| 9,499,627 B2 | 11/2016 | Podack et al. |
| 9,556,277 B2 | 1/2017 | Classon et al. |
| 9,683,998 B2 | 6/2017 | Arch et al. |
| 9,834,606 B2 | 12/2017 | Li et al. |
| 9,839,670 B2 | 12/2017 | Podack et al. |
| 9,896,511 B2 | 2/2018 | Siegel et al. |
| 2002/0078757 A1 | 6/2002 | Hines et al. |
| 2003/0017518 A1 | 1/2003 | Lam et al. |
| 2003/0129189 A1 | 7/2003 | Yu et al. |
| 2003/0166871 A1 | 9/2003 | Barbas et al. |
| 2003/0198640 A1 | 10/2003 | Yu et al. |
| 2004/0123343 A1 | 6/2004 | La et al. |
| 2008/0177048 A1 | 7/2008 | Gagnon |
| 2009/0187005 A1 | 7/2009 | Gagnon |
| 2009/0317388 A1 | 12/2009 | Burkly et al. |
| 2011/0217310 A1 | 9/2011 | Siegel et al. |
| 2011/0243951 A1 | 10/2011 | Podack et al. |
| 2012/0014950 A1 | 1/2012 | Migone et al. |
| 2012/0079611 A1 | 3/2012 | Shih et al. |
| 2012/0315282 A1 | 12/2012 | Bedinger et al. |
| 2014/0255302 A1 | 9/2014 | Poulton et al. |
| 2015/0031972 A1 | 1/2015 | Freeman et al. |
| 2016/0009802 A1 | 1/2016 | Longman et al. |
| 2016/0060330 A1 | 3/2016 | Presta |
| 2016/0200833 A1 | 7/2016 | Amann et al. |
| 2016/0333104 A1 | 11/2016 | Poulton et al. |
| 2017/0081400 A1 | 3/2017 | Poulton et al. |
| 2017/0096491 A1 | 4/2017 | Classon et al. |
| 2018/0021696 A1 | 1/2018 | Wang et al. |
| 2018/0052175 A1 | 2/2018 | Arch et al. |
| 2018/0078611 A1 | 3/2018 | Podack et al. |
| 2018/0086840 A1 | 3/2018 | Attinger et al. |
| 2018/0179285 A1 | 6/2018 | Bennett et al. |
| 2018/0186888 A1 | 7/2018 | Siegel et al. |
| 2018/0319889 A1 | 11/2018 | Croft et al. |

FOREIGN PATENT DOCUMENTS

| | | |
|---|---|---|
| WO | WO-9614328 A1 | 5/1996 |
| WO | WO-0066608 A1 | 11/2000 |
| WO | WO-0204643 A1 | 1/2002 |
| WO | WO-2004035537 A2 | 4/2004 |
| WO | WO-2004050836 A2 | 6/2004 |
| WO | WO-2006017173 A1 | 2/2006 |
| WO | WO-2007005608 A2 | 1/2007 |
| WO | WO-2008106579 A2 | 9/2008 |
| WO | WO-2012161856 A1 | 11/2012 |
| WO | WO-2014106602 A1 | 7/2014 |
| WO | WO-2014160463 A1 | 10/2014 |
| WO | WO-2017077715 A1 | 5/2017 |
| WO | WO-2017106383 A1 | 6/2017 |
| WO | WO-2017196663 A1 | 11/2017 |
| WO | WO-2018081074 A1 | 5/2018 |

OTHER PUBLICATIONS

Al-Iazikani et al., Standard conformations for the canonical structures of immunoglobulins. J. Molec. Biol. 273:927-948, 1997.

Australian Patent Application No. 2014241162 Office Action dated Apr. 16, 2018.

Barrett et al., Constitutive TL1A Expression under Colitogenic Condition Modulates the Severity and Location of Gut Mucosal Inflammation and Induces Fibrostenosis, American Journal of Pathology, 2012, vol. 180(2), pp. 636-649.

Bauer et al., A genetic enrichment for mutations constructed by oligodeoxynucleotide-directed mutagenesis. Gene, 37:73-81, 1985.

Benedict et al., Immunoglobulin Kappa light chain variable region, Partial (Mus musculus). GenBank: AAD39789.1, Jul. 26, 2016, 1 page.

Bird et al., Single-chain antigen-binding proteins. Science, 242:423-42, 1988.

Brennan et al. Preparation of bispecific antibodies by chemical recombination of monoclonal immunoglobulin G$_{1}$ fragments. Science 229:81-83, 1985.

Brummell et al. Probing the combining site of an anti-carbohydrate antibody by saturation-mutagenesis: Role of the heavy-chain CDR3 residues. Biochem. 32: 1180-1187, 1993.

Burks et al., In vitro scanning saturation mutagenesis of an antibody binding pocket. Proc. Natl. Acad. Sci. USA 94:412-417, 1997.

Clarke et al. An anti-TL1A antibody for the treatment of asthma and inflammatory bowel disease. MAbs 10(4):664-677 (2018).

Craik, Charles. Use of oligonucleotides for site-specific mutagenesis. BioTechniques 1985 :12-19, 1985.

Erpenbeck et al. Segmental allergen challenge in patients with atopic asthma leads to increased IL-9 expression in bronchoalveolar lavage fluid lymphocytes. J Allergy Clin Immunol 111(6):1319-1327, 2003.

Fang et al. Essential role of TNF receptor superfamily 25 (TNFRS25) in the development of allergic lung inflammation. J Exp Med 205(5):1037-1048, 2008.

Fitzpatrick, LR, Novel Pharmacological Approaches for Inflammatory Bowl Disease: Targeting Key Intracellular Pathways and the IL-23/IL-17 Axis, International Journal of Inflammation, vol. 2012, pp. 1-8.

Hodgson, John. Making monoclonals in microbes. Bio/Technology 9:421-425, 1991.

Holliger and Hudson. Engineered antibody fragments and the rise of single domains. Nat. Biotechnol. 23(9):1126-36, 2005.

Hsu et al. The tale of TL1A in inflammation. Mucosal Immunol 4(4):368-370, 2011.

Huse et al. Generation of a large combinatorial library of the immunoglobulin repertoire in phage lambda. Science 246:1275-1281, 1989.

Huston et al. Protein engineering of antibody binding sites: Recovery of specific activity in an anti-digoxin single-chain Fv analogue produced in *Escherichia coli*. Proc. Natl. Acad. Sci. USA 85:5879-5883, 1988.

Jones et al. Replacing the complementarity-determining regions in a human antibody with those from a mouse. Nature 321:522-525, 1986.

Kim et al. Effects of IL-9 blockade on chronic airway inflammation of murine asthma models. Allergy: Eur J Allergy Clin Immunol Suppl 96(67):448, Nov. 2012.

Kim et al. Effects of interleukin-9 blockade on chronic airway inflammation in murine asthma models. Allergy Asthma Immunol Res 5(4):197-206, 2013.

Kobayashi et al. Tryptophan H33 plays an important role in pyrimidine (6-4) pyrimidone photoproduct binding by a high-affinity antibody. Protein Eng. 12(10):879-884, 1999.

Koga et al., Transanal Delivery of Angiotensin Converting Enzyme Inhibitor Prevents Colonic Fibrosis in a Mouse Colitis Model: Development of a Unique Mode of Treatment, Surgery, 144(2):259-268, 2008.

Kohler and Milstein, Derivation of specific antibody-producing tissue culture and tumor lines by cell fusion. Eur. J. Immunol. 6: 511-519, 1976.

(56) References Cited

OTHER PUBLICATIONS

Meylan et al., The TNF-family cytokine TL1A drives IL-13 dependent small intestinal inflammation. Muscosal Immunol., 4(2):172-185, 2011.

Morimoto et al. Single-step purification of F(ab')2 fragments of mouse monoclonal antibodies (immunoglobulins G1) by hydrophobic interaction high performance liquid chromatography using TSKgel Phenyl-5PW. Journal of Biochemical and Biophysical Methods 24:107-117, 1993.

Parente et al., Bowel Ultrasound in Assessment of Crohn's Disease and Detection of Related Small Bowel Strictures: A Prospective Comparative Study Versus X Ray and Intraoperative Findings, Gut, 50: 490-495, 2002.

PCT/US2009/069541 International Search Report dated Mar. 4, 2010.

PCT/US2017/058019 International Search Report and Written Opinion dated Feb. 15, 2018.

Pinchuk et al., Human Colonic Myofibroblast Promote Expansion of CD4+ CD25high Foxp3+ Regulatory T Cells, Gastroenterology, 140(7):2019-2030, pp. 1-19, and p. 8, 2011.

Queen et al. A humanized antibody that binds to the interleukin 2 receptor. Proc. Natl. Acad Sci USA 86:10029-10032, 1989.

Riechmann et al. Reshaping human antibodies for therapy. Nature, 332.6162 (1988): 323-7.

Rothe et al., The human combinatorial antibody library HuCAL GOLD combines diversification of all six CDRs according to the natural immune system with a novel display method for efficient selection of high-affinity antibodies. J. Mol. Bio. 376:1182-1200, 2008.

Shin et al. Reversal of murine colitis and fibrosis by neutralizing TL1A antibody: potential novel therapy to alter natural history of Crohn's disease. Gastroenterol 142(5):584, Abstract #357, 2012.

Shih et at, Constitutive TL1A (TNFSF15) Expression on Lymphoid or Myeloid Cells Leads to Mild Intestinal Inflammation and Fibrosis, PLOS One, 6(1), pp. 1-16, 2011.

Bamias et al. Circulating levels of TNF-like cytokine 1A (TL1A) and its decoy receptor 3 (DcR3) in rheumatoid arthritis. Clin Immunol 129:249-255, 2008.

Spinelli et al., Intestinal Fibrosis in Crohn's Disease: Medical Treatment or Surgery?, Current Drug Targets, 11(2):242-248, 2010.

Strober et at, Proinflammatoly Cytokines in Pathogenesis of Inflammatory Bowel Diseases, Gastroenterology, 140(6):1756-1767, 2011.

Takedatsu et al., TL 1A (TNFSF15) regulates the development of chronic colitis by modulating both T helper (TH)1 and TH17 activation. Gastroenterology vol. 135:552-567 (2008).

Tomlinson I. and Holliger P. Methods for generating multivalent and bispecific antibody fragments. Methods Enzymol 326:461-479, 2000.

U.S. Appl. No. 15/245,875 Office Action dated Jun. 12, 2018.

Verhoeyen et al. Reshaping human antibodies: Grafting an antilysozyme activity. Science 239:1534-1536, 1988.

Walder et al. Oligodeoxynucleotide-directed mutagenesis using the yeast transformation system. Gene 42:133-139, 1986.

Ward et al. Binding activities of a repertoire of single immunoglobulin variable domains secreted from *Escherichia coli*. Nature 334:544-54, 1989.

* cited by examiner

Panel A

5C3D11

Panel B

9E12E5

NEUTRALIZING ANTI-TL1A MONOCLONAL ANTIBODIES

CROSS-REFERENCE

This application claims priority to U.S. Provisional Application 62/413,188 filed Oct. 26, 2016, the entirety of which is incorporated by reference herein.

SEQUENCE LISTING

The instant application contains a Sequence Listing which has been submitted electronically in ASCII format and is hereby incorporated by reference in its entirety. Said ASCII copy, created on Oct. 23, 2017, is named 52388-728_201_SL.txt and is 33,920 bytes in size.

BACKGROUND

Inflammatory bowel disease (IBD) refers to a collection of intestinal disorders causing inflammatory conditions in the gastrointestinal tract. The primary types of IBD are ulcerative colitis (UC) and Crohn's Disease (CD). These diseases are prevalent, with about 1.86 billion people diagnosed globally with UC, and about 1.3 million people diagnosed globally with CD. Unfortunately, there are a limited number of therapies available for IBD patients, and the development of new therapeutics has been hampered by sub-optimal results in clinical trials. Accordingly, there is a need for novel therapeutics to treat IBD.

SUMMARY

The present disclosure provides antibodies useful for the treatment of IBD. In one aspect, provided is an antibody or antigen-binding fragment that specifically binds to a TL1A polypeptide. In some embodiments, the antibody or antigen-binding fragment comprises: a heavy chain comprising complementarity determining regions (CDRs) of SEQ ID NOs: 6-8 and a light chain comprising complementarity determining regions (CDRs) of SEQ ID NOs: 14-16. In some embodiments, the antibody or antigen-binding fragment comprises: a heavy chain comprising complementarity determining regions (CDRs) of SEQ ID NOs: 22-24 and a light chain comprising complementarity determining regions (CDRs) of SEQ ID NOs: 30-32. In some embodiments, the antibody or antigen-binding fragment is: a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, or a combination thereof. Further embodiments provide for pharmaceutical compositions comprising a therapeutically effective amount of the antibody or antigen-binding fragment, and a pharmaceutically acceptable carrier. Further embodiments provide for a method of treating inflammatory bowel disease in a subject in need thereof, comprising administering to the subject a therapeutically effective amount of the antibody or an antigen-binding fragment. In some embodiments, the inflammatory bowel disease comprises Crohn's Disease, ulcerative colitis, medically refractive-ulcerative colitis, or a combination thereof. In some embodiments, prior to administering the antibody or antigen-binding fragment to the subject, the subject over-expresses TL1A. In some embodiments, the subject comprises a risk variant associated with the inflammatory bowel disease.

In another aspect, provided herein is a polypeptide comprising: one or more complementarity determining regions selected from the group consisting of SEQ ID NO: 6, SEQ ID NO: 7, SEQ ID NO: 8, SEQ ID NO: 14, SEQ ID NO: 15, SEQ ID NO: 16, SEQ ID NO: 22, SEQ ID NO: 23, SEQ ID NO: 24, SEQ ID NO: 30, SEQ ID NO: 31, and SEQ ID NO: 32.

In another aspect, provided herein is an antibody or antigen binding fragment that binds to the same region of human TL1A as a reference antibody comprising the heavy chain complementarity determining regions (CDRs) of SEQ ID NOs: 6-8 and the light chain complementarity determining regions (CDRs) of SEQ ID NOs: 14-16. In some embodiments, the reference antibody comprises a heavy chain variable domain of SEQ ID NO: 5 and a light chain variable domain of SEQ ID NO: 13. In some embodiments, the antibody or antigen-binding fragment is: a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, or a combination thereof. Further embodiments provide for a pharmaceutical composition comprising a therapeutically effective amount of the antibody or antigen-binding fragment, and a pharmaceutically acceptable carrier. Further embodiments provide for a method of treating inflammatory bowel disease in a subject in need thereof, comprising administering to the subject a therapeutically effective amount of the antibody or an antigen-binding fragment. In some embodiments, the inflammatory bowel disease comprises Crohn's Disease, ulcerative colitis, medically refractive-ulcerative colitis, or a combination thereof. In some embodiments, prior to administering the antibody or antigen-binding fragment to the subject, the subject over-expresses TL1A. In some embodiments, the subject comprises a risk variant associated with the inflammatory bowel disease.

In another aspect, provided herein is an antibody or antigen binding fragment that binds to the same region of human TL1A as a reference antibody comprising the heavy chain complementarity determining regions (CDRs) of SEQ ID NOs: 22-24 and the light chain complementarity determining regions (CDRs) of SEQ ID NOs: 30-32. In some embodiments, the reference antibody comprises a heavy chain variable domain of SEQ ID NO: 21 and a light chain variable domain of SEQ ID NO: 29. In some embodiments, the antibody or antigen-binding fragment is: a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, or a combination thereof. Further embodiments provide for a pharmaceutical composition comprising a therapeutically effective amount of the antibody or antigen-binding fragment, and a pharmaceutically acceptable carrier. Further embodiments provide for a method of treating inflammatory bowel disease in a subject in need thereof, comprising administering to the subject a therapeutically effective amount of the antibody or an antigen-binding fragment. In some embodiments, the inflammatory bowel disease comprises Crohn's Disease, ulcerative colitis, medically refractive-ulcerative colitis, or a combination thereof. In some embodiments, prior to administering the antibody or antigen-binding fragment to the subject, the subject over-expresses TL1A. In some embodiments, the subject comprises a risk variant associated with the inflammatory bowel disease.

In another aspect, provided herein is a composition comprising a peptide having SEQ ID NO: 7. In some embodiments, the composition further comprises one or more peptides selected from SEQ ID NOs: 6, 8, and 14-16. Further embodiments provide for a method of treating a subject having an inflammatory bowel disease, the method comprising administering to the subject an effective amount of the composition.

In another aspect, provided herein is a composition comprising a peptide having SEQ ID NO: 23. In some embodiments, the composition further comprises one or more peptides selected from SEQ ID NOs: 22, 24 and 30-32. Further embodiments provide for a method of treating a subject having an inflammatory bowel disease, the method comprising administering to the subject an effective amount of the composition.

In another aspect, provided herein is a method of treating an inflammatory bowel disease in a subject in need thereof, the method comprising administering to the subject an effective amount of an anti-TL1A antibody, provided that the subject comprises one or more risk variants at the TNFSF15 locus, and provided that the anti-TL1A antibody comprises a heavy chain comprising complementarity determining regions (CDRs) of SEQ ID NOs: 6-8 and a light chain comprising complementarity determining regions (CDRs) of SEQ ID NOs: 14-16. In some embodiments, the anti-TL1A antibody is: a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, or a combination thereof. In some embodiments, the inflammatory bowel disease comprises Crohn's Disease, ulcerative colitis, medically refractive-ulcerative colitis, or a combination thereof.

In another aspect, provided herein is a method of treating an inflammatory bowel disease in a subject in need thereof, the method comprising administering to the subject an effective amount of an anti-TL1A antibody, provided that the subject comprises one or more risk variants at the TNFSF15 locus, and provided that the anti-TL1A antibody comprises a heavy chain comprising complementarity determining regions (CDRs) of SEQ ID NOs: 22-24 and a light chain comprising complementarity determining regions (CDRs) of SEQ ID NOs: 30-32. In some embodiments, the anti-TL1A antibody is: a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, or a combination thereof. In some embodiments, the inflammatory bowel disease comprises Crohn's Disease, ulcerative colitis, medically refractive-ulcerative colitis, or a combination thereof.

In another aspect, provided herein is a method of treating an inflammatory bowel disease in a subject in need thereof, the method comprising administering to the subject an effective amount of an anti-TL1A antibody, provided that the subject over-express TL1A, and provided that the anti-TL1A antibody comprises a heavy chain comprising complementarity determining regions (CDRs) of SEQ ID NOs: 6-8 and a light chain comprising complementarity determining regions (CDRs) of SEQ ID NOs: 14-16. In some embodiments, the anti-TL1A antibody is: a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, or a combination thereof. In some embodiments, the inflammatory bowel disease comprises Crohn's Disease, ulcerative colitis, medically refractive-ulcerative colitis, or a combination thereof.

In another aspect, provided herein is a method of treating an inflammatory bowel disease in a subject in need thereof, the method comprising administering to the subject an effective amount of an anti-TL1A antibody, provided that the subject over-express TL1A, and provided that the anti-TL1A antibody comprises a heavy chain comprising complementarity determining regions (CDRs) of SEQ ID NOs: 22-24 and a light chain comprising complementarity determining regions (CDRs) of SEQ ID NOs: 30-32. In some embodiments, the anti-TL1A antibody is: a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, or a combination thereof. In some embodiments, the inflammatory bowel disease comprises Crohn's Disease, ulcerative colitis, medically refractive-ulcerative colitis, or a combination thereof.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
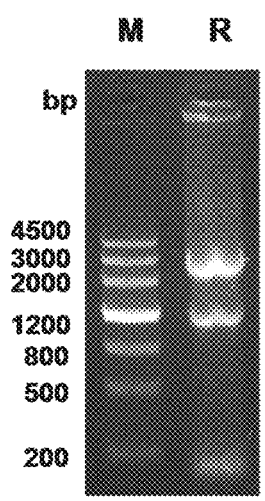
FIG. 1 depicts agarose gel electrophoresis of total RNA from the hybridoma 684842-3 (5C3D11). DNA marker, Marker III, is shown in Lane M and Total RNA of 684842-3 is shown in Lane R.

Tumor necrosis factor-like protein 1A (TL1A) has been associated with the development and severity of severe colitis and Crohn's Disease. In addition, preclinical and human genetic association data suggests that TL1A is a potential therapeutic target in Crohn's disease. The present disclosure describes neutralizing antibodies against TL1A and offers a novel therapeutic for the treatment of IBD.

All references cited herein are incorporated by reference in their entirety as though fully set forth. Unless defined otherwise, technical and scientific terms used herein have the same meaning as commonly understood by one of ordinary skill in the art. Singleton et al., *Dictionary of Microbiology and Molecular Biology* 3$^{rd}$ ed., Revised, J. Wiley & Sons (New York, N.Y. 2006); and Sambrook and Russel, *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application. For references on how to prepare antibodies, see D. Lane, *Antibodies: A Laboratory Manual* 2$^{nd}$ ed. (Cold Spring Harbor Press, Cold Spring Harbor N.Y., 2013); Kohler and Milstein, (1976) Eur. J. Immunol. 6: 511; Queen et al. U.S. Pat. No. 5,585,089; and Riechmann et al., Nature 332: 323 (1988); U.S. Pat. No. 4,946,778; Bird, Science 242:423-42 (1988); Huston et al., Proc. Natl. Acad. Sci. USA 85:5879-5883 (1988); Ward et al., Nature 334:544-54 (1989); Tomlinson I. and Holliger P. (2000) Methods Enzymol, 326, 461-479; Holliger P. (2005) Nat. Biotechnol. Sep;23 (9): 1126-36).

One skilled in the art will recognize many methods and materials similar or equivalent to those described herein, which could be used to practice embodiments described herein. Indeed, this specification is not limited to the methods and materials described. Non-limiting definitions of select terms used herein are provided below.

"IBD" refers to Inflammatory Bowel Disease and includes, without limitation, Crohn's Disease, Ulcerative colitis and Medically Refractive Ulcerative colitis.

"CD", "UC", and "MR-UC" refer to Crohn's Disease, Ulcerative colitis, and Medically Refractive-Ulcerative colitis, respectively.

"TL1A" refers to TNF-like protein 1A.

"TNFSF15" refers to Tumor necrosis factor superfamily member 15, and is sometimes interchangeable with TL1A.

"SNP" refers to single nucleotide polymorphism.

"Risk variant" and "risk allele" refer to an allele whose presence is associated with an increase in susceptibility to an inflammatory bowel disease, including but not limited to Crohn's Disease, Ulcerative colitis, and Medically Refractive-Ulcerative colitis, relative to an individual who does not have the risk variant or risk allele.

"Protective variant" and "protective allele" refer to an allele whose presence is associated with a decreased probability of developing inflammatory bowel disease, including but not limited to Crohn's Disease, Ulcerative colitis, and Medically Refractive-Ulcerative colitis, relative to an individual who does not have the protective variant or protective allele. The protective variant is more frequently present in healthy individuals compared to individuals diagnosed with inflammatory bowel disease.

"Protective" and "protection" as used with respect to the presence of particular specific variants or alleles refers to a decrease in susceptibility to IBD, including but not limited to CD, UC, and MR-UC.

"Risk" as used with respect to the presence of specific variants or alleles refers to an increase in susceptibility to IBD, including but not limited to CD, UC, and MR-UC.

"Biological sample" refers to any biological material from which nucleic acid and/or protein molecules can be found. As non-limiting examples, the term material encompasses whole blood, plasma, serum, saliva, cheek swab, and any other bodily fluid or tissue.

"IC" refers to immune complex.

"PBMC" refers to a peripheral blood mononuclear cell.

"Anti-TL1A therapy" refers to any reagent that suppresses a response to TL1A and/or inhibits TL1A signaling, including, without limitation, inhibition of any molecular signaling step from the TL1A ligand through its receptor to various upstream and/or downstream molecular targets. The anti-TL1A therapy can include the use of a small molecule; a nucleic acid such as siRNA, shRNA, and miRNA; a nucleic acid analogue such as PNA, pc-PNA, and LNA; an aptamer; a ribosome; a peptide; a protein; an avimer; an antibody, or variants and fragments thereof; and/or combinations of any thereof.

The term "antibody" refers to an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, and Fv fragments), single chain Fv (scFv) mutants, a CDR-grafted antibody, multispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" is inclusive of an "antigen-binding fragment" that refers to a portion of an antibody having antigenic determining variable regions of an antibody. Examples of antibody fragments include, but are not limited to Fab, Fab', F(ab')$_2$, and Fv fragments, linear antibodies, single chain antibodies, and multispecific antibodies formed from antibody fragments.

The term "monoclonal antibody" refers to a homogeneous antibody population involved in the highly specific recognition and binding of a single antigenic determinant, or epitope. This is in contrast to polyclonal antibodies that typically include different antibodies directed against different antigenic determinants.

The term "humanized antibody" refers to forms of non-human (e.g., murine) antibodies having specific immunoglobulin chains, chimeric immunoglobulins, or fragments thereof that contain minimal non-human (e.g., murine) sequences. For example, a humanized antibody comprises less than about 40% non-human sequence in the variable region. In some cases, a humanized antibody comprises less than about 20% non-human sequence in a full length antibody sequence. In some cases, humanized antibodies are human immunoglobulins in which residues from the complementarity determining region (CDR) are replaced by residues from the CDR of a non-human species (e.g., mouse, rat, rabbit, hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). Examples of methods used to generate humanized antibodies are described in U.S. Pat. No. 5,225,539.

The term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising human light chain and human heavy chain polypeptides.

The term "chimeric antibodies" refers to antibodies wherein the sequence of the immunoglobulin molecule is derived from two or more species. Typically, the variable region of both light and heavy chains corresponds to the variable region of antibodies derived from one species of mammals (e.g., mouse, rat, rabbit, etc) with the desired specificity, affinity, and capability while the constant regions are homologous to the sequences in antibodies derived from another (usually human) to avoid eliciting an immune response in that species.

Each heavy and light chain is composed of a "variable region" of said heavy or light chain and a "constant region" of said heavy or light chain. The heavy chain and light chain regions may be further divided into hypervariable regions referred to as complementarity-determining regions (CDRs) and interspersed with conserved regions referred to as framework regions (FR). Each heavy chain and light chain region thus consists of three CDRs and four FRs, which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining region within antibody variable sequences and contributes to the formation of the antigen-binding site of antibodies. Techniques for determining CDRs are known in the art (e.g., Kabat et al. Sequences of Proteins of Immunological Interest, (5th ed., 1991, National Institutes of Health, Bethesda Md.; and Al-lazikani et al (1997) J. Molec. Biol. 273:927-948).

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate antigen binding are well-known in the art (see, e.g., Brummell et al., Biochem. 32: 1180-1 187 (1993); Kobayashi et al. Protein Eng. 12(10):879-884 (1999); and Burks et al. Proc. Natl. Acad. Sci. USA 94:412-417 (1997)).

That an antibody "specifically binds" to a protein means that the antibody reacts or associates more frequently, more rapidly, with greater duration, with greater affinity, or with some combination of the above to the protein than with alternative substances, including unrelated proteins. Because of the sequence identity between homologous proteins in different species, specific binding can include an antibody that recognizes a particular protein such as TL1A in more than one species. An antibody may in certain embodiments, bind to multiple targets bound by the same antigen-binding site on the antibody or the antibody may be bispecific and comprise at least two antigen-binding sites with differing specificities.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as fusion with another polypeptide and/or conjugation, e.g., with a labeling component. Also included within the definition are, for example, polypeptides containing one or more analogs of an amino acid (for example, unnatural amino acids, etc.), as well as other modifications known in the art.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as, but not limited to methylated nucleotides and their analogs or non-nucleotide components. Modifications to the nucleotide structure may be imparted before or after assembly of the polymer. A polynucleotide may be further modified after polymerization, such as by conjugation with a labeling component.

The term "vector" means a construct, which is capable of delivering, and preferably expressing, one or more gene(s) and/or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure. In some cases, "substantially pure" refers to material which is at least 50% pure (i.e., free from contaminants), at least 90% pure, at least 95% pure, at least 98% pure, or at least 99% pure.

The terms "identical" or percent "identity" in the context of two or more nucleic acids or polypeptides, refer to two or more sequences or subsequences that are the same or have a specified percentage of nucleotides or amino acid residues that are the same, when compared and aligned for maximum correspondence. The percent identity may be measured using sequence comparison software or algorithms or by visual inspection. Various algorithms and software are known in the art that may be used to obtain alignments of amino acid or nucleotide sequences. Such algotithm/software programs include, but are not limited to NBLAST, XBLAST, Gapped BLAST, BLAST-2, WU-BLAST-2, ALIGN, ALIGN-2 or Megalign (DNASTAR).

Terms such as "treating" or "treatment" or "to treat" or "alleviating" or "to alleviate" refer to therapeutic treatment and/or prophylactic or preventative measures, wherein the object is to prevent or slow down (lessen) the targeted pathologic condition, prevent the pathologic condition, pursue or obtain good overall survival, or lower the chances of the individual developing the condition even if the treatment is ultimately unsuccessful. Thus, those in need of treatment include those already with the disorder; those prone to have the disorder; and those in whom the disorder is to be prevented.

The term "subject" refers to any animal (e.g., a mammal), including, but not limited to humans, non-human primates, rodents, and domestic and game animals, which is to be the recipient of a particular treatment. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Typically, the terms "subject" and "patient" are used interchangeably herein in reference to a human subject. In various embodiments, a subject can be one who has been previously diagnosed with or identified as suffering from or having a condition in need of treatment. In various other embodiments, the subject previously diagnosed with or identified as suffering from or having a condition may or may not have undergone treatment for a condition. In yet other embodiments, a subject can also be one who has not been previously diagnosed as having a condition (i.e., a subject who exhibits one or more risk factors for a condition). A "subject in need" of treatment for a particular condition can be a subject having that condition, diagnosed as having that condition, or at risk of developing that condition.

The term "therapeutically effective amount" refers to an amount of an antibody, polypeptide, polynucleotide, small organic molecule, or other drug effective to "treat" a disease or disorder in a subject or mammal. In some cases, the therapeutically effective amount of the drug reduces the severity of IBD symptoms, including CD and UC/MR-UC symptoms. These include, but are not limited to, diarrhea, fever, fatigue, abdominal pain, abdominal cramping, inflammation, ulceration, nausea, vomiting, bleeding, blood in stool, reduced appetite, weight loss, and a combination thereof.

In one aspect, the disclosure describes the identification of two neutralizing anti-human TL1A monoclonal antibodies and five neutralizing humanized anti-human TL1A monoclonal antibodies. These antibodies neutralize the activity of TL1A in vitro and recognize both soluble and membrane bound TL1A.

TL1A (TNFSF15) is a TNF family member expressed mainly by endothelial cells, macrophages, and dendritic cells (DC). Its expression is induced by immune complex (IC) and cytokines. TL1A receptor DR3 is mainly expressed on T cells and NKT cells. In vitro, TL1A has been shown to enhance both human and mouse T cell proliferation and cytokine production. In vivo, TL1A transgenic mice developed IBD phenotype similar to human Crohn's. In addition, treatment of recombinant TL1A protein also exacerbated colitis in mdr1−/− mice.

The present disclosure provides neutralizing anti-TL1A monoclonal antibodies useful for treating IBD, CD, UC and MR-UC. In some cases, these anti-TL1A antibodies are used to treat a specific inflammatory bowel disease (IBD) patient population. Related polypeptides and polynucleotides, compositions comprising the anti-TL1A antibodies, and methods of making the anti-TL1A antibodies are also provided. Methods of using the novel anti-TL1A antibodies for treatment are further provided.

Anti-TL1A Antibodies

Various embodiments provide antibodies that specifically bind to TL1A. In some embodiments, the antibodies specifically bind to soluble TL1A. In some embodiments, the antibodies specifically bind to membrane bound TL1A. The full-length amino acid (aa) sequence for the TL1A antibody "5C3D11" comprises: SEQ ID NO: 5 (heavy chain) and SEQ ID NO: 13 (light chain), as shown in Table 1. In various embodiments, the TL1A antibody comprises SEQ ID NO: 5 and SEQ ID NO: 13. A monomeric TL1A antibody comprises two instances of SEQ ID NO: 5 and SEQ ID NO: 13. In various embodiments, the TL1A antibody comprises SEQ ID NO: 6, SEQ ID NO: 7, SEQ ID NO: 8, SEQ ID NO: 14, SEQ ID NO: 15 and SEQ ID NO: 16, as shown in Table 1. In some embodiments, the TL1A antibody comprises at least one or any combination of SEQ ID NO: 6, SEQ ID NO: 7, SEQ ID NO: 8, SEQ ID NO: 14, SEQ ID NO: 15 and SEQ ID NO: 16.

The full-length nucleotide (nt) sequence for the TL1A antibody "5C3D11" is encoded by nucleic acid sequences comprising SEQ ID NO: 1 (heavy chain) and SEQ ID NO: 9 (light chain). In various embodiments, the TL1A antibody is encoded by nucleic acid sequences comprising SEQ ID NO: 1 and SEQ ID NO: 9, as shown in Table 1. A monomeric TL1A antibody is encoded by two instances of nucleic acid sequences comprising SEQ ID NO: 1 and SEQ ID NO: 9. In various embodiments, the TL1A antibody is encoded by nucleic acid sequences comprising SEQ ID NO: 2, SEQ ID NO: 3, SEQ ID NO: 4, SEQ ID NO: 10, SEQ ID NO: 11 and SEQ ID NO: 12, as shown in Table 1. In some embodiments, the TL1A antibody is encoded by at least one or any combination of nucleic acid sequences comprising SEQ ID NO: 2, SEQ ID NO: 3, SEQ ID NO: 4, SEQ ID NO: 10, SEQ ID NO: 11 and SEQ ID NO: 12.

The full-length amino acid (aa) sequence for the TL1A antibody "9E12E5" comprises: SEQ ID NO: 21 (heavy chain) and SEQ ID NO: 29 (light chain), as shown in Table 1. In various embodiments, the TL1A antibody comprises SEQ ID NO: 21 and SEQ ID NO: 29. A monomeric TL1A antibody comprises two instances of SEQ ID NO: 21 and SEQ ID NO: 29. In various embodiments, the TL1A antibody comprises SEQ ID NO: 22, SEQ ID NO: 23, SEQ ID NO: 24, SEQ ID NO: 30, SEQ ID NO: 31 and SEQ ID NO: 32, as shown in Table 1. In some embodiments, the TL1A antibody comprises at least one or any combination of SEQ ID NO: 22, SEQ ID NO: 23, SEQ ID NO: 24, SEQ ID NO: 30, SEQ ID NO: 31 and SEQ ID NO: 32.

The full-length nucleotide (nt) sequence for the TL1A antibody "9E12E5" is encoded by nucleic acid sequences comprising SEQ ID NO: 17 (TL1A heavy chain) and SEQ ID NO: 25 (TL1A light chain), as shown in Table 1. In various embodiments, the TL1A antibody is encoded by nucleic acid sequences comprising SEQ ID NO: 17 and SEQ ID NO: 25. A monomeric TL1A antibody is encoded by two instances of nucleic acid sequences comprising SEQ ID NO: 17 and SEQ ID NO: 25. In various embodiments, the TL1A antibody is encoded by nucleic acid sequences comprising SEQ ID NO: 18, SEQ ID NO: 19, SEQ ID NO: 20, SEQ ID NO: 26, SEQ ID NO: 27 and SEQ ID NO: 28, as shown in Table 1. In some embodiments, the TL1A antibody is encoded by at least one or any combination of nucleic acid sequences comprising SEQ ID NO: 18, SEQ ID NO: 19, SEQ ID NO: 20, SEQ ID NO: 26, SEQ ID NO: 27 and SEQ ID NO: 28.

TABLE 1

Nucleotide and Amino Acid sequences for 5C3D11 and 9E12E5.

| Antibody | Sequence Type | Size | Leader Sequence | Sequence | SEQ ID No: |
|---|---|---|---|---|---|
| | 5C3D11 | | | | |
| Heavy Chain | DNA | 405 bp | FR1-CDR1-FR2-CDR2-FR3-CDR3-FR4 | ATGAAATGCAGCTGGGTTATCTTCTTCCTGATGGCAGTGGTTACA GGGGTCAATTCAGAGGTTCAGCTGCAGCAGTCTGGGGCAGAACTT GTGAAGCCAGGGGCCTCAGTCAAGTTGTCCTGCACAGCTTCTGGC TTCGACATTCAAGACACCTATATGCACTGGGTCAAGCAGAGGCCT GAACAGGGCCTGGAGTGGATTGGAAGGATTGATCCTGCGAGTGGA CATACTAAATATGACCCGAAGTTCCAGGTCAAGGCCACTATAACA ACGGACACATCCTCCAACACAGCCTACCTGCAGCTCAGCAGCCTG ACATCTGAGGACACTGCCGTCTATTACTGTTCTAGATCGGGGGGC CTACCTGATGTCTGGGGCGCAGGGACCACGGTCACCGTCTCCTCA | 1 |
| | | | CDR1 | GACACCTATATGCAC | 2 |
| | | | CDR2 | AGGATTGATCCTGCGAGTGGACATACTAAATATGACCCGAAGTTC CAGGTC | 3 |
| | | | CDR3 | TCGGGGGGCTACCTGATGTC | 4 |
| Heavy Chain | Amino Acid | 135 aa | FR1-CDR1-FR2-CDR2-FR3-CDR3-FR4 | MKCSWVIFFLMAVVTGVNS*EVQLQQSGAELVKPGASVKLSCTASG FDIQ*DTYMH*WVKQRPEQGLEWIG*RIDPASGHTKYDPKFQV*KATIT TDTSSNTAYLQLSSLTSEDTAVYYCSRS*GGLPDV*WGAGTTVTVSS* | 5 |
| | | | CDR1 | DTYMH | 6 |
| | | | CDR2 | RIDPASGHTKYDPKFQV | 7 |
| | | | CDR3 | SGGLPDV | 8 |
| Light Chain | DNA | 384 bp | FR1-CDR1-FR2-CDR2-FR3-CDR3-FR4 | ATGGATTTTCAAGTGCAGATTTTCAGCTTCCTGCTAATCAGTGCT TCAGTCATAATGTCCAGAGGACAAATTGTTCTCTCCCAGTCTCCT GCAATCCTGTCTGCATCTCCAGGGGAGAAGGTCACAATGACTTGC AGGGCCAGCTCAAGTGTAAGTTACATGTACTGGTACCAGCAGAAG CCTGGATCCTCCCCCAAACCCTGGATTTTATGCCACATCCAACCT GGCTTCTGGAGTCCCTGATCGCTTCAGTGGCAGTGGGTCTGGGAC CTCTTACTCTCTCACAATCAGCAGAGTGGAGGCTGAAGATGCTGC CACTTATTACTGCCAGCAGTGGAGTGGTAACCCACGGACGTTCGG TGGAGGCACCAAGCTGGAAATCAAA | 9 |
| | | | CDR1 | AGGGCCAGCTCAAGTGTAAGTTACATGTAC | 10 |
| | | | CDR2 | GCCACATCCAACCTGGCTTCT | 11 |
| | | | CDR3 | CAGCAGTGGAGTGGTAACCCACGGACG | 12 |
| Light Chain | Amino Acid | 128 aa | FR1-CDR1-FR2-CDR2-FR3-CDR3-FR4 | MDFQVQIFSFLLISASVIMSRGQIVLSQSPAILSASPGEKVTMTC RASSSVSYMY*WYQQKPGSSPKPWIY*ATSNLAS*GVPDRFSGSGSGT SYSLTISRVEAEDAATYYC*QQWSGNPRT*FGGGTKLEIK* | 13 |
| | | | CDR1 | RASSSVSYMY | 14 |
| | | | CDR2 | ATSNLAS | 15 |
| | | | CDR3 | QQWSGNPRT | 16 |
| | 9E12E5 | | | | |
| Heavy Chain | DNA | 405 bp | FR1-CDR1-FR2-CDR2-FR3-CDR3-FR4 | ATGGGATGGAGCTGGGTCTTTCTCTTCCTCCTGTCAGTGACTGCA GGTGTCCACTCCCAGGTTCACCTGCAGCAGTCTGGACCTGAACTG GTAAAGCCTGGGGCTTCAGTGAAGTTGTCCTGCAAGGCTTCTGGC TACACCTTCACAAAGTATGATATAAACTGGGTGAGGCAGAGGCCT GAACAGGGACTTGAGTGGATTGGATGGATTTTTCCTGGAGATGGT AGAACTGACTACAATGAAGTTCAAGGGTAAGGCCACACTGACT ACAGACAAATCCTCCAGCACAGCCTACATGGAGGTCAGCAGGCTG ACATCTGAGGACTCTGCTGTCTATTTCTGTGCAACATATGGCCCC GCTATGGACTACTGGGGTCAAGGAACCCTCAGTCACCGTCGCCTCA | 17 |
| | | | CDR1 | AAGTATGATATAAAC | 18 |
| | | | CDR2 | TGGATTTTTCCTGGAGATGGTAGAACTGACTACAATGAAGTTCA AGGGT | 19 |
| | | | CDR3 | TATGGCCCCGCTATGGACTA | 20 |

TABLE 1-continued

Nucleotide and Amino Acid sequences for 5C3D11 and 9E12E5.

| Antibody | Sequence Type | Size | Leader Sequence | Sequence | SEQ ID No: |
|---|---|---|---|---|---|
| Heavy Chain | Amino Acid | 135 aa | FR1-CDR1-<br>FR2-CDR2-<br>FR3-CDR3-<br>FR4 | MGWSWVFLFLLSVTAGVHS*QVHLQQSGPELVKPGASVKLSCKASG*<br>*YTFT*KYDIN*WVRQRPEQGLEWIG**WIFPGDGRTDYNEKFKG**KATLT*<br>*TDKSSSTAYMEVSRLTSEDSAVYFCAR**YGPAMDY**WGQGTSVTVAS* | 21 |
| | | | CDR1 | KYDIN | 22 |
| | | | CDR2 | WIFPGDGRTDYNEKFKG | 23 |
| | | | CDR3 | YGPAMDY | 24 |
| Light Chain | DNA | 393 bp | FR1-CDR1-<br>FR2-CDR2-<br>FR3-CDR3-<br>FR4 | ATGAAGTTGCCTGTTAGGCTGTTGGTGCTGATGTTCTGGATTCCT<br>GCTTCCAGCAGT*GATGTTTTGATGACCCAAACTCCACTCTCCCTG*<br>*CCTGTCAGTCTTGGAGATCAAGCCTCCATCTCTTGC*AGATCTAGT*<br>*CAGACCATTGTACATAGTAATGGAGACACCTATTTAGAC**TGGTTC*<br>*CTGCAGAAACCAGGCCAGTCTCCAAAGCTCCTGATCTA**AAAGTT*<br>*TCCAACCGATTTTCT**GGGGTCCCAGACAGGTTCAGTGGCAGTGGA*<br>*TCAGGGACAGATTTCACACTCAAGATCAGCAGAGTGGAGGCTGAG*<br>*GATCTGGGAGTTTATTACTGC**TTTCAAGGTTCACATGTTCCGTAC*<br>*ACG**TTCGGAGGGGGACCAAGCTGGAAATAAAA* | 25 |
| | | | CDR1 | AGATCTAGTCAGACCATTGTACATAGTAATGGAGACACCTATTTA<br>GAC | 26 |
| | | | CDR2 | AAAGTTTCCAACCGATTTTCT | 27 |
| | | | CDR3 | TTTCAAGGTTCACATGTTCCGTACACG | 28 |
| Light Chain | Amino Acid | 131 aa | FR1-CDR1-<br>FR2-CDR2-<br>FR3-CDR3-<br>FR4 | MKLPVRLLVLMFWIPASSS*DVLMTQTPLSLPVSLGDQASISC**RSS*<br>*QTIVHSNGDTYLDWFLQKPGQSPKLLIYKVSNRFS**GVPDRFSGSG*<br>*SGTDFTLKISRVEAEDLGVYYC**FQGSHVPYT**FGGGTKLEIK* | 29 |
| | | | CDR1 | RSSQTIVHSNGDTYLD | 30 |
| | | | CDR2 | KVSNRFS | 31 |
| | | | CDR3 | FQGSHVPYT | 32 |

In various embodiments, the anti-TL1A antibody binds specifically to the same region of TL1A or binds specifically to a region of TL1A that overlaps with the region of TL1A to which an antibody comprising a heavy chain variable region encoded by SEQ ID NO:1 and a light chain variable region encoded by SEQ ID NO: 9 binds specifically. In various other embodiments, the anti-TL1A antibody binds specifically to the same region of TL1A or binds specifically to a region of TL1A that overlaps with the region of TL1A to which an antibody comprising a heavy chain comprising the sequence of SEQ ID NO: 5 and a light chain comprising the sequence of SEQ ID NO: 13 binds specifically. In other embodiments, the anti-TL1A antibody binds specifically to the same region of TL1A or binds specifically to a region of TL1A that overlaps with the region of TL1A to which an antibody comprising a heavy chain variable region encoded by SEQ ID NO:17 and a light chain variable region encoded by SEQ ID NO: 25 binds specifically. In certain other embodiments, the anti-TL1A antibody binds specifically to the same region of TL1A or binds specifically to a region of TL1A that overlaps with the region of TL1A to which an antibody comprising a heavy chain comprising SEQ ID NO: 21 and a light chain comprising SEQ ID NO: 29 binds specifically.

Further embodiments provide polypeptides, including, but not limited to, antibodies that specifically bind to TL1A, that comprise one, two, three, four, five, six, seven, eight, nine, ten, eleven and/or twelve of the CDRs of 5C3D11 and/or 9E12E5 (see Table 1, and Tables 2 and 3 of Example 1 and 2 below). In certain embodiments, the polypeptides comprise the heavy chain CDRs of 5C3D11 (SEQ ID NOs: 6, 7, and 8) and/or 9E12E5 (SEQ ID NOs: 22, 23, and 24), the light chain CDRs of 5C3D11 (SEQ ID NOs: 14, 15, and 16) and/or 9E12E5 (SEQ ID NOs: 30, 31, and 32), or combinations thereof. In certain other embodiments, the heavy chain CDR(s) are contained within a heavy chain variable region and/or the light chain CDR(s) are contained within a light chain variable region. In some embodiments, polypeptides comprising one of the individual light chains or heavy chains described herein, as well as polypeptides (e.g., antibodies) comprising both a light chain and a heavy chain are also provided. In some embodiments, the anti-TL1A antibody comprises the heavy chains and light chains of 5C3D11. In other embodiments, the anti-TL1A antibody comprises the heavy chains and light chains of 9E12E5. In certain embodiments, each CDR in the anti-TL1A antibody comprises up to four (i.e., 0, 1, 2, 3, or 4) conservative amino acid substitutions per CDR.

In various embodiments, the anti-TL1A antibody or fragment has a binding affinity to TL1A of at least about $1E^{-7}$, $1E^{-8}$, $1E^{-9}$, $1E^{-10}$, or $1E^{-11}$. In some cases, the binding affinity is from about $1E^{-9}$ to about $1E^{-11}$. For example, in some cases the binding affinity is about $7.90E^{-11}$. In various embodiments, the anti-TL1A antibody or fragment has a binding affinity to TL1A of about $7.90E^{-9}$ to about $7.90E^{-10}$. In various embodiments, the anti-TL1A antibody or fragment has a binding affinity to TL1A of about $7.90E^{-10}$ to about $7.90E^{-12}$. In various embodiments, the anti-TL1A antibody or fragment has a binding affinity to TL1A of about $7.90E^{-12}$ to about $7.90E^{-13}$.

In various embodiments, the anti-TL1A antibody or fragment has a binding affinity to TL1A of about $5.20E^{-11}$. In various embodiments, the anti-TL1A antibody or fragment has a binding affinity to TL1A of about $5.20E^{-9}$ to about $5.20E^{10}$. In various embodiments, the anti-TL1A antibody or fragment has a binding affinity to TL1A of about $5.20E^{-10}$ to $5.20E^{-12}$. In various embodiments, the anti-TL1A antibody or fragment has a binding affinity to TL1A of about $5.20E^{-12}$ to $5.20E^{-13}$.

Various embodiments provide for an anti-TL1A antibody that binds to the same region of a TL1A protein or portion thereof as a reference antibody, e.g., any anti-TL1A antibody described herein. In some embodiments, the reference antibody comprises the heavy chain CDRs of SEQ ID NOs: 6-8 and the light chain CDRs of SEQ ID NOs: 14-16. In some cases, the reference antibody comprises a heavy chain variable domain of SEQ ID NO: 5 and a light chain variable domain of SEQ ID NO: 13. In some embodiments, the reference antibody comprises the heavy chain CDRs of SEQ ID NOs: 22-24 and the light chain CDRs of SEQ ID NOs: 30-32. In some cases, the reference antibody comprises a heavy chain variable domain of SEQ ID NO: 21 and a light chain variable domain of SEQ ID NO: 29. In some cases, the reference antibody is 5C3D11. In some cases, the reference antibody is 9E12E5.

Non-limiting methods for determining whether an anti-TL1A antibody (i.e. test antibody) binds to the same region of a TL1A protein or portion thereof as an antibody described herein are provided. An exemplary embodiment comprises a competition assay. For instance, the method comprises determining whether the test antibody can compete with binding between the reference antibody and the TL1A protein or portion thereof, or determining whether the reference antibody can compete with binding between the test antibody and the TL1A protein or portion thereof. Exemplary methods include use of surface plasmon resonance to evaluate whether an anti-TL1A antibody can compete with the binding between TL1A and another anti-TL1A antibody. In some cases, surface plasmon resonance is utilized in the competition assay. Non-limiting methods are described in Example 9 and Example 10.

Methods of Generating Antibodies

Various embodiments provide for an antibody that is generated using a polypeptide or a nucleotide sequence. In some embodiments, the antibody is a monoclonal antibody. In some embodiments, the antibody is a human antibody or a humanized antibody. In some embodiments, the antibody is an antibody fragment. For example, the antibody is a Fab. In some embodiments, the antibody is a chimeric antibody.

The antibodies described herein can be assayed for specific binding by any method known in the art. The immunoassays which can be used include, but are not limited to, competitive and non-competitive assay systems using techniques such as BIAcore analysis, FACS analysis, immunofluorescence, immunocytochemistry, Western blots, radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, e.g., Ausubel et al., eds, 1994, Current Protocols in Molecular Biology, Vol. 1, John Wiley & Sons, Inc., New York).

In various embodiments, the antibody is an antagonist of a TL1A receptor, such as, but not limited to, DR3 and TR6/DcR3. In certain embodiments, the antibody inhibits at least about 10%, at least about 20%, at least about 30%, at least about 50%, at least about 75%, at least about 90%, or about 100% of one or more activity of the bound TL1A receptor.

In various embodiments, monoclonal antibodies are prepared using methods known in the art, such as, but not limited to the hybridoma method, where a host animal is immunized, as described above to elicit the production by lymphocytes of antibodies that will specifically bind to an immunizing antigen (Kohler and Milstein (1975) Nature 256:495). Hybridomas produce monoclonal antibodies directed specifically against a chosen antigen. The monoclonal antibodies are purified from the culture medium or ascites fluid by techniques known in the art, when propagated either in vitro or in vivo.

In some embodiments, monoclonal antibodies are made using recombinant DNA methods as described in U.S. Pat. No. 4,816,567. The polynucleotides encoding a monoclonal antibody are isolated from mature B-cells or hybridoma cells. The isolated polynucleotides encoding the heavy and light chains are then cloned into suitable expression vectors, which when transfected into host cells (e.g., *E. coli* cells, simian COS cells, Chinese hamster ovary (CHO) cells, or myeloma cells) generate monoclonal antibodies. The polynucleotide(s) encoding a monoclonal antibody can further be modified in a number of different manners using recombinant DNA technology to generate alternative antibodies.

In various embodiments, "chimeric antibodies", a molecule in which different portions are derived from different animal species, such as those having a variable region derived from a murine monoclonal antibody and a human immunoglobulin constant region (e.g., humanized antibodies) can be generated. Chimeric antibodies can be produced using various techniques known in the art (see Morrison et al., Proc. Natl. Acad. Sci. 81:851-855 (1984); Neuberger et al., Nature 312:604-608 (1984); Takeda et al., Nature 314:452-454 (1985)).

In some embodiments, the anti-TL1A monoclonal antibody is a humanized antibody, to reduce antigenicity and HAMA (human anti-mouse antibody) responses when administered to a human subject. Humanized antibodies can be produced using various techniques known in the art. For example, an antibody is humanized by (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody (see, e.g., U.S. Pat. Nos. 5,585,089; 6,835,823; 6,824,989). In various embodiments, a humanized antibody can be further optimized to decrease potential immunogenicity, while maintaining functional activity, for therapy in humans.

In some embodiments, the humanized anti-TL1A antibody comprises a heavy chain variable domain of any of SEQ ID NOS: 35-39. In some embodiments, the humanized anti-TL1A antibody comprises a light chain variable domain of any of SEQ ID NOS: 40-44. In some cases, the humanized anti-TL1A antibody comprises a heavy chain variable domain having SEQ ID NO: 35, and a light chain variable domain having SEQ ID NO: 40. In some cases, the humanized anti-TL1A antibody comprises a heavy chain variable domain having SEQ ID NO: 36, and a light chain variable domain having SEQ ID NO: 41. In some cases, the humanized anti-TL1A antibody comprises a heavy chain variable domain having SEQ ID NO: 37, and a light chain variable domain having SEQ ID NO: 42. In some cases, the humanized anti-TL1A antibody comprises a heavy chain variable domain having SEQ ID NO: 38, and a light chain variable domain having SEQ ID NO: 43. In some cases, the humanized anti-TL1A antibody comprises a heavy chain variable domain having SEQ ID NO: 39, and a light chain variable domain having SEQ ID NO: 44.

In certain embodiments, the anti-TL1A antibody is a human antibody. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). A human antibody can be selected from a phage library. Techniques for the generation and use of antibody phage libraries are described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018.

Humanized antibodies can also be made in transgenic mice containing human immunoglobulin loci that are capable, upon immunization, of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016. A humanized antibody may also be obtained by a novel genetic engineering approach that enables production of affinity-matured human-like polyclonal antibodies in large animals such as, for example, rabbits and mice. (See, e.g. U.S. Pat. No. 6,632,976).

A fully humanized antibody may be created by first designing a variable region amino acid sequence that contains non-human, e.g., rodent-derived CDRs, embedded in human-derived framework sequences. The non-human CDRs provide the desired specificity. Accordingly, in some cases these residues are included in the design of the reshaped variable region essentially unchanged. In some cases, modifications should therefore be restricted to a minimum and closely watched for changes in the specificity and affinity of the antibody. On the other hand, framework residues in theory can be derived from any human variable region. A human framework sequences should be chosen, which is equally suitable for creating a reshaped variable region and for retaining antibody affinity, in order to create a reshaped antibody which shows an acceptable or an even improved affinity. The human framework may be of germline origin, or may be derived from non-germline (e.g. mutated or affinity matured) sequences. Genetic engineering techniques well known to those in the art, for example, but not limited to, phage display of libraries of human antibodies, transgenic mice, human-human hybridoma, hybrid hybridoma, B cell immortalization and cloning, single-cell RT-PCR or HuRAb Technology, may be used to generate a humanized antibody with a hybrid DNA sequence containing a human framework and a non-human CDR. Methods to obtain "humanized antibodies" are well known to those skilled in the art. (e.g., U.S. Pat. Nos. 5,861,155, 6,479,284, 6,407,213, 5,624,821, US2003166871, US20020078757, Queen et al., Proc. Natl. Acad Sci USA, 86:10029-10032 (1989) and Hodgson et al., Bio/Technology, 9:421 (1991)).

Chimeric, humanized and human antibodies are typically produced by recombinant expression. Recombinant polynucleotide constructs typically include an expression control sequence operably linked to the coding sequences of antibody chains, including naturally-associated or heterologous promoter regions. In certain embodiments, it may be desirable to generate amino acid sequence variants of these humanized antibodies, particularly where these improve the binding affinity or other biological properties of the antibody.

In certain embodiments, an antibody fragment is used to treat and/or ameliorate IBD. Various techniques are known for the production of antibody fragments. Generally, these fragments are derived via proteolytic digestion of intact antibodies (for example Morimoto et al., 1993, Journal of Biochemical and Biophysical Methods 24:107-117; Brennan et al., 1985, Science, 229:81). Fab, Fv, and scFv antibody fragments can all be expressed in and secreted from E. coli or other host cells, thus allowing the production of large amounts of these fragments. Other techniques for the production of antibody fragments will be apparent to the skilled practitioner.

According to the present disclosure, techniques can be adapted for the production of single-chain antibodies specific to TL1A (see e.g., U.S. Pat. No. 4,946,778). In addition, methods can be adapted for the construction of Fab expression libraries (see e.g., Huse, et al., Science 246:1275-1281 (1989)) to allow rapid and effective identification of monoclonal Fab fragments with the desired specificity for TL1A, or derivatives, fragments, analogs or homologs thereof. Antibody fragments may be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

Also provided herein are modified antibodies comprising any type of variable region that provides for the association of the antibody with TL1A. Those skilled in the art will appreciate that the modified antibodies may comprise antibodies (e.g., full-length antibodies or immunoreactive fragments thereof) in which at least a fraction of one or more of the constant region domains has been deleted or otherwise altered so as to provide desired biochemical characteristics such as decreasing TL1A. In certain embodiments, the variable regions in both the heavy and light chains are altered by at least partial replacement of one or more CDRs and, if necessary, by partial framework region replacement and sequence changing. In some embodiments, the replaced CDRs may be derived from an antibody of the same class, subclass, from an antibody of a different class, for instance, from an antibody from a different species and/or a combination thereof. In some embodiments, the constant region of the modified antibodies will comprise a human constant region. Modifications to the constant region compatible with this disclosure comprise additions, deletions or substitutions of one or more amino acids in one or more domains.

In various embodiments, the expression of an antibody or antigen-binding fragment thereof as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. In other embodiments, the antibody or antigen-fragment thereof as described herein may be transfected into the host.

In some embodiments, the expression vectors are transfected into the recipient cell line for the production of the chimeric, humanized, or composite human antibodies described herein. In various embodiments, mammalian cells can be useful as hosts for the production of antibody proteins, which can include, but are not limited to cells of fibroblast origin, such as Vero (ATCC CRL 81) or CHO-K1 (ATCC CRL 61) cells, HeLa cells and L cells. Exemplary eukaryotic cells that can be used to express polypeptides include, but are not limited to, COS cells, including COS 7 cells; 293 cells, including 293-6E cells; CHO cells, including CHO-S and DG44 cells; PER.C6™ cells (Crucell); and NS0 cells. In some embodiments, a particular eukaryotic host cell is selected based on its ability to make desired post-translational modifications to the heavy chains and/or light chains.

A number of suitable host cell lines capable of secreting intact heterologous proteins have been developed in the art, and include, but are not limited to CHO cell lines, various COS cell lines, HeLa cells, L cells and multiple myeloma cell lines.

An expression vector carrying a chimeric, humanized, or composite human antibody construct, antibody or antigen-binding fragment thereof as described herein can be introduced into an appropriate host cell by any of a variety of suitable means, depending on the type of cellular host including, but not limited to transformation, transfection, lipofection, conjugation, electroporation, direct microinjection, and microprojectile bombardment, as known to one of ordinary skill in the art. Expression vectors for these cells can include expression control sequences, such as an origin of replication sites, a promoter, an enhancer and necessary processing information sites, such as ribosome binding sites, RNA splice sites, polyadenylation sites, and transcriptional terminator sequences.

In various embodiments, yeast can also be utilized as hosts for the production of the antibody molecules or peptides described herein. In various other embodiments, bacterial strains can also be utilized as hosts for the production of the antibody molecules or peptides described herein. Examples of bacterial strains include, but are not limited to *E. coli, Bacillus* species, enterobacteria, and various *Pseudomonas* species.

In some embodiments, one or more antibodies or antigen-binding fragments thereof as described herein can be produced in vivo in an animal that has been engineered (transgenic) or transfected with one or more nucleic acid molecules encoding the polypeptides, according to any suitable method. For production of transgenic animals, transgenes can be microinjected into fertilized oocytes, or can be incorporated into the genome of embryonic stem cells, and the nuclei of such cells transferred into enucleated oocytes. Once expressed, antibodies can be purified according to standard procedures of the art, including HPLC purification, column chromatography, gel electrophoresis and the like (see generally, Scopes, Protein Purification (Springer-Verlag, N.Y., 1982)).

Once expressed in the host, the whole antibodies, antibody-fragments (e.g., individual light and heavy chains), or other immunoglobulin forms of the present disclosure can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, N.Y., 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized or composite human antibody can then be used therapeutically or in developing and performing assay procedures, immunofluorescent stainings, etc. See generally, Vols. I & II Immunol. Meth. (Lefkovits & Pernis, eds., Acad. Press, N.Y., 1979 and 1981).

Various embodiments provide for a genetic construct comprising a nucleic acid encoding an anti-TL1A antibody or fragment provided herein. Genetic constructs of the antibody can be in the form of expression cassettes, which can be suitable for expression of the encoded anti-TL1A antibody or fragment. The genetic construct may be introduced into a host cell with or without being incorporated in a vector. For example, the genetic construct can be incorporated within a liposome or a virus particle. Alternatively, a purified nucleic acid molecule can be inserted directly into a host cell by methods known in the art. The genetic construct can be introduced directly into cells of a host subject by transfection, infection, electroporation, cell fusion, protoplast fusion, microinjection or ballistic bombardment.

Various embodiments provide a recombinant vector comprising the genetic construct of an antibody provided herein. The recombinant vector can be a plasmid, cosmid or phage. The recombinant vectors can include other functional elements; for example, a suitable promoter to initiate gene expression.

Various embodiments provide a host cell comprising a genetic construct and/or recombinant vector described herein.

Polypeptides and Polynucleotides

Various embodiments provide for a polypeptide comprising one or more complementarity determining regions selected from the group consisting of SEQ ID NO: 6, SEQ ID NO: 7, SEQ ID NO: 8, SEQ ID NO: 14, SEQ ID NO: 15, SEQ ID NO: 16, SEQ ID NO: 22, SEQ ID NO: 23, SEQ ID NO: 24, SEQ ID NO: 30, SEQ ID NO: 31; and SEQ ID NO: 32. In various embodiments, the polypeptide comprises 2, 3, 4, 5, 6, 7, 8, 9, 10, 11 or 12 of these complementarity determining regions.

In various embodiments, the antibody is generated using a polypeptide or a polynucleotide.

The polypeptides can be recombinant polypeptides, or synthetic polypeptides comprising an antibody, or fragment thereof, against TL1A. When specifically noted, polypeptides can be natural polypeptides. It will be recognized in the art that some amino acid sequences can be varied without significant effect of the structure or function of the protein. Thus, further provided are variations of the polypeptides which show substantial activity or which include regions of an antibody, or fragment thereof, against a TL1A protein. Such modifications include deletions, insertions, inversions, repeats, and type substitutions.

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest.

Various host systems are also advantageously employed to express recombinant protein. Examples of suitable mammalian host cell lines include the COS-7 lines of monkey kidney cells, and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine (SEQ ID NO: 45), maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography. Recombinant protein produced in bacterial culture can be isolated. Methods known in the art for purifying antibodies and other proteins also include, for example, those described in U.S. Patent Publication No. 2008/0177048, and 2009/0187005.

One of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as He, Val, Leu, or Ala for one another), or substitution of one polar residue for another (such as between Lys and Arg; Glu and Asp; or Gin and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained.

Particular conservative substitutions include, for example; Ala into Gly or into Ser; Arg into Lys; Asn into Gin or into H is; Asp into Glu; Cys into Ser; Gin into Asn; Glu into Asp; Gly into Ala or into Pro; His into Asn or into Gin; lie into Leu or into Val; Leu into lie or into Val; Lys into Arg, into Gin or into Glu; Met into Leu, into Tyr or into lie; Phe into Met, into Leu or into Tyr; Ser into Thr; Thr into Ser; Trp into Tyr; Tyr into Trp; and/or Phe into Val, into lie or into Leu.

In some embodiments, the antibody and/or antigen-binding fragment thereof described herein can be a variant of a sequence described herein, e.g., a conservative substitution variant of an antibody polypeptide. In some embodiments, the variant is a conservatively modified variant. A "variant," as referred to herein with respect to a polypeptide, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity, e.g., antigen-specific binding activity for the relevant target polypeptide.

Alterations of the native amino acid sequence can be accomplished by any of a number of techniques known to one of skill in the art. Mutations can be introduced at particular loci or by oligonucleotide-directed site-specific mutagenesis procedures. Techniques for making such alterations are very well established and include, for example, those disclosed by Walder et al. (Gene 42: 133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462.

In certain embodiments, provided are polynucleotides that encode a polypeptide that specifically binds TL1A or a fragment thereof. For example, provided is a polynucleotide comprising a nucleic acid sequence that encodes an antibody to TL1A or encodes a fragment of such an antibody. The polynucleotides can be in the form of RNA or in the form of DNA. DNA includes cDNA, genomic DNA, and synthetic DNA; and can be double-stranded or single-stranded, and if single stranded can be the coding strand or non-coding (anti-sense) strand. In certain embodiments, the polynucleotides are isolated. In certain embodiments, the polynucleotides are substantially pure.

Further provided is a polynucleotide comprising a sequence selected from the group consisting of SEQ ID NOs: 1, 9, 17, 25 and a combination thereof. Also provided are variants of the herein described polynucleotides encoding, for example, fragments, analogs, and derivatives.

Nucleic acid molecules encoding amino acid sequence variants of antibodies are prepared by a variety of methods known in the art. These methods include, but are not limited to, preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including but not limited to, blunt-ended or staggered-ended termini for ligation and restriction enzyme digestion. Techniques for such manipulations are disclosed, e.g., by Maniatis et al., Molecular Cloning, Lab. Manual (Cold Spring Harbor Lab. Press, NY, 1982 and 1989), and can be used to construct nucleic acid sequences which encode a monoclonal antibody molecule or antigen-binding region.

In some embodiments, a nucleic acid encoding an antibody or antigen-binding fragment thereof as described herein is comprised by a vector. In some of the aspects described herein, a nucleic acid sequence encoding an antibody or antigen-binding fragment thereof as described herein, or any module thereof, is operably linked to a vector. The term "vector," as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an antibody or antigen-binding portion thereof as described herein in place of non-essential viral genes. The vector and/or particle may be utilized for the purpose of transferring any nucleic acids into cells either in vitro or in vivo. Numerous forms of viral vectors are known in the art.

By "recombinant vector," it is meant that the vector includes a heterologous nucleic acid sequence, or "transgene" that is capable of expression in vivo.

In certain embodiments, provided are isolated polynucleotides comprising polynucleotides having a nucleotide sequence at least 80% identical, at least 85% identical, at least 90% identical, at least 95% identical, and in some embodiments, at least 96%, 97%, 98% or 99% identical to a polynucleotide encoding a polypeptide comprising an antibody, or fragment thereof, to TL1A described herein.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

In some embodiments, genes are fused to create a desired sequence. Each fused gene is assembled in or inserted into an expression vector, which is transfected into a recipient. The transfected recipient cells are cultured under conditions that permit expression of the incorporated genes and the expressed immunoglobulin chains or intact antibodies or fragments are recovered from the culture. In some embodiments, the fused genes encoding the antibody, antigen-binding fragment thereof, are assembled in separate expression vectors that are then used to co-transfect a recipient cell.

Pharmaceutical Compositions, Administration and Dosage

The anti-TL1A antibodies provided are useful in a variety of applications including, but not limited to, therapeutic treatment methods, such as the treatment of IBD. The methods of use may be in vitro, ex vivo, or in vivo methods. In certain embodiments, the anti-TL1A antibody is an antagonist for TL1A receptors.

In certain embodiments, the disease treated with anti-TL1A antibody or TL1A receptor antagonist is IBD, CD, UC and/or MR-UC.

In various embodiments, the pharmaceutical compositions are formulated for delivery via any route of administration. "Route of administration" may refer to any administration pathway known in the art, including but not limited to aerosol, nasal, oral, transmucosal, transdermal or parenteral.

"Transdermal" administration may be accomplished using a topical cream or ointment or by means of a transdermal patch.

"Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release.

Via the topical route, the pharmaceutical compositions are formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication.

Via the ocular route, they may be in the form of eye drops.

In various embodiments, an agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. In particular embodiments, compounds used herein are administered orally, intravenously or intramuscularly to a patient having IBD, CD, UC and/or MR-UC.

The pharmaceutical compositions can also contain any pharmaceutically acceptable carrier. "Pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

In various embodiments, provided are pharmaceutical compositions including a pharmaceutically acceptable excipient along with a therapeutically effective amount of an anti-TL1A antibody. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. The active ingredient can be mixed with excipients which are pharmaceutically acceptable and compatible with the active ingredient and in amounts suitable for use in the therapeutic methods described herein. Such excipients may be solid, liquid, semisolid, or, in the case of an aerosol composition, gaseous. Suitable excipients are, for example, starch, glucose, lactose, sucrose, gelatin, malt, rice, flour, chalk, silica gel, sodium stearate, glycerol monostearate, talc, sodium chloride, dried skim milk, water, saline, dextrose, propylene glycol, glycerol, ethanol, mannitol, polysorbate or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts. Pharmaceutically acceptable salts include the acid addition salts formed with inorganic acids such as, for example, hydrochloric or phosphoric acids, organic acids, for example, acetic, tartaric or mandelic, salts formed from inorganic bases such as, for example, sodium, potassium, ammonium, calcium or ferric hydroxides, and salts formed from organic bases such as isopropylamine, trimethylamine, 2-ethylamino ethanol, histidine, procaine and the like. Liquid compositions can contain liquid phases in addition to and in the exclusion of water, for example, glycerin, vegetable oils such as cottonseed oil, and water-oil emulsions. Physiologically tolerable carriers are well known in the art. The amount of an active agent (i.e. antibody or fragment thereof) used that will be effective in the treatment of a particular disorder or condition will depend on the nature of the disorder or condition, and can be determined by one of skill in the art with standard clinical techniques.

The pharmaceutical compositions can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins Pa., USA) (2000).

Typical dosages of an effective anti-TL1A antibody can be as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biological samples obtained, or the responses observed in the appropriate animal models.

For the treatment of the disease, the appropriate dosage of an antibody depends on the type of disease to be treated, the severity and course of the disease, the responsiveness of the disease, whether the antibody is administered for therapeutic or preventative purposes, previous therapy, and patient's clinical history. The dosage can also be adjusted by the individual physician in the event of any complication and at the discretion of the treating physician. The administering physician can determine optimum dosages, dosing methodologies and repetition rates. The TL1A antibody can be administered one time or over a series of treatments lasting from several days to several months, or until a cure is effected or a diminution of the disease state is achieved (e.g., treatment or amelioration of IBD). The duration of treatment depends upon the subject's clinical progress and responsiveness to therapy. In certain embodiments, dosage is from 0.01 μg to 100 mg per kg of body weight, and can be given once or more daily, weekly, monthly or yearly. For systemic administration, subjects can be administered a therapeutic amount, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

Methods of Treatment

Various embodiments provide for methods of treating inflammatory bowel disease (IBD), comprising administering an anti-TL1A antibody described herein to a subject in need thereof. In some embodiments, the subject comprises one or more risk variants.

In various embodiments, provided herein is a method of treating inflammatory bowel disease (IBD) in a subject in need thereof, comprising: administering to the subject a therapeutically effective amount of an antibody or an antigen-binding fragment that specifically binds TL1A, wherein the antibody or antigen-binding fragment is selected from the group consisting of: (a) a heavy chain comprising SEQ ID NO: 5 and a light chain comprising SEQ ID NO: 13; (b) a heavy chain comprising SEQ ID NO: 21 and a light chain comprising SEQ ID NO: 29; (c) the heavy chain complementarity determining regions (CDRs) of SEQ ID NOs: 6-8 and the light chain complementarity determining regions (CDRs) of SEQ ID NOs: 14-16; (d) the heavy chain complementarity determining regions (CDRs) of SEQ ID NOs: 22-24 and the light chain complementarity determining regions (CDRs) of SEQ ID NOs: 30-32; (e) the heavy chain of SEQ ID NOs: 5 and/or 21; (f) the light chain of SEQ ID NOs: 13 and/or 29; (g) the heavy chain complementarity determining regions (CDRs) of SEQ ID NOs: 6-8 and/or SEQ ID NOs: 22-24; (h) the light chain complementarity determining regions (CDRs) of SEQ ID NOs: 14-16 and/or SEQ ID NOs: 30-32; and (i) combinations thereof.

In various embodiments, inflammatory bowel disease (IBD) is Crohn's Disease, ulcerative colitis, and/or medically refractive-ulcerative colitis.

In various embodiments, the antibody is a monoclonal antibody. In some embodiments, the antibody is a human antibody. In various embodiments, the antibody is a humanized antibody. In various embodiments, the antibody is a neutralizing antibody.

In various other embodiments, the subject is determined to have an increased TL1A expression. In some embodiments, the administration of a therapeutically effective amount of an anti-TL1A antibody causes a decrease in TL1A in the subject treated.

In various embodiments, the antibody or antigen-binding fragment is selected from the group consisting of: (a) a heavy chain comprising SEQ ID NO: 5 and a light chain comprising SEQ ID NO: 13; (b) the heavy chain complementarity determining regions (CDRs) of SEQ ID NOs: 6-8 and the light chain complementarity determining regions (CDRs) of SEQ ID NOs: 14-16; (c) the heavy chain of SEQ ID NO: 5; (d) the light chain of SEQ ID NO: 13; (e) the heavy chain complementarity determining regions (CDRs) of SEQ ID NOs: 6-8; (f) the light chain complementarity determining regions (CDRs) of SEQ ID NOs: 14-16; and (g) combinations thereof.

In various other embodiments, the antibody or antigen-binding fragment is selected from the group consisting of: (a) a heavy chain comprising SEQ ID NO: 21 and a light chain comprising SEQ ID NO: 29; (b) the heavy chain complementarity determining regions (CDRs) of SEQ ID NOs: 22-24 and the light chain complementarity determining regions (CDRs) of SEQ ID NOs: 30-32; (c) the heavy chain of SEQ ID NO: 21; (d) the light chain of SEQ ID NO: 29; (e) the heavy chain complementarity determining regions (CDRs) of SEQ ID NOs: 22-24; (f) the light chain complementarity determining regions (CDRs) of SEQ ID NOs: 30-32; and (g) combinations thereof.

In various embodiments, the antibody or antigen-binding fragment is encoded by a nucleic acid having a sequence selected from the group consisting of SEQ ID NO: 1, SEQ ID NO: 9, SEQ ID NO: 17, SEQ ID NO: 25 and combinations thereof.

In various other embodiments, the antibody or antigen-binding fragment is encoded by a nucleic acid having a sequence selected from the group consisting of: (a) the heavy chain complementarity determining regions (CDRs) of SEQ ID NOs: 2-4 and the light chain complementarity determining regions (CDRs) of SEQ ID NOs: 10-12; (b) the heavy chain complementarity determining regions (CDRs) of SEQ ID NOs: 18-20 and the light chain complementarity determining regions (CDRs) of SEQ ID NOs: 26-28; (c) the heavy chain of SEQ ID NOs: 1 and/or 17; (d) the light chain of SEQ ID NOs: 9 and/or 25; (e) the heavy chain complementarity determining regions (CDRs) of SEQ ID NOs: 2-4 and/or SEQ ID NOs: 18-20; (f) the light chain complementarity determining regions (CDRs) of SEQ ID NOs: 10-12 and/or SEQ ID NOs: 26-28; and (g) combinations thereof.

In various aspects, the anti-TL1A antibody is administered to the subject for treatment. In various other embodiments, the anti-TL1A antibody is administered in a series of treatments. In some embodiments, the anti-TL1A antibody and a second IBD treatment may be administered in any order or concurrently. In selected embodiments, the anti-TL1A antibody will be administered to patients that have previously undergone treatment with the second IBD treatment. In certain other embodiments, the anti-TL1A antibody and the second IBD treatment will be administered substantially simultaneously or concurrently. For example, a subject may be given the anti-TL1A antibody while undergoing a course of treatment with the second IBD treatment. In certain embodiments, the anti-TL1A antibody will be administered within 1 year of the treatment with the second IBD treatment. In certain alternative embodiments, the anti-TL1A antibody will be administered within 10, 8, 6, 4, or 2 months of any treatment with the second IBD treatment. In certain other embodiments, the anti-TL1A antibody will be administered within 4, 3, 2, or 1 week of any treatment with the second IBD treatment. In some embodiments, the anti-TL1A antibody will be administered within 5, 4, 3, 2, or 1 days of any treatment with the second IBD treatment. It will further be appreciated that the two treatments may be administered to the subject within a matter of hours or minutes (i.e., simultaneously).

Other IBD treatments include, but are not limited to 1) anti-inflammatory drugs (e.g., Aminosalicylates such as, but not limited to sulfasalazine Azulfidine, 5-aminosalicylates, Mesalamine, Asacol, Lialda, Rowasa, Canasa, balsalazide Colazal and olsalazine, Dipentum); 2) corticosteroids (e.g., prednisone and hydrocortisone); 3) immune system suppressors (e.g., Azathioprine, Azasan, Imuran, mercaptopurine, Purinethol, Purixan, Cyclosporine, Gengraf, Neoral and Sandimmune, Infliximab, Remicade, adalimumab, Humira, golimumab, and Simponi, tumor necrosis factor (TNF)-alpha inhibitors (e.g., Infliximab), Methotrexate, Rheumatrex, Natalizumab, Tysabri, vedolizumab, Entyvio, Ustekinumab and Stelara; 4) Antibiotics (e.g., Metronidazole, Flagyl, Ciprofloxacin, Cipro); 5) Anti-diarrheal medications (e.g., fiber supplements—Metamucil or Citrucel) or loperamide; 6) Pain relievers (e.g., Tylenol, ibuprofen, naproxen sodium and diclofenac sodium); and 7) Surgery (e.g., removal of the colon, partial digestive tract removal, colectomy, proctocolectomy and/or strictureplasty). In some embodiments, these IBD treatments may be administered in combination with the anti-TL1A antibody. Treatment with an antibody can occur prior to, concurrently with, or subsequent to administration of an IBD treatment. Combined administration can include co-administration, either in a single pharmaceutical formulation or using separate formulations, or consecutive administration in either order but generally within a time period such that all active agents can exert their biological activities simultaneously. Any dosing schedules for such IBD treatments can also be used as determined by the skilled practitioner.

In some embodiments, the second IBD treatment comprises an antibody. Thus, treatment can involve the combined administration of antibodies provided herein with other antibodies against additional IBD-associated antigens, such as, but not limited to tumor necrosis factor (TNF)-alpha. Combined administration can include co-administration, either in a single pharmaceutical formulation or using separate formulations, or consecutive administration in either order but generally within a time period such that all active agents can exert their biological activities simultaneously.

Kits

Further provided is a kit to treat IBD (e.g., CD, UC and/or MR-UC). The kit comprises of the antibodies described herein, which can be used to perform the methods described herein. The kit is useful for practicing the inventive method of providing treatment to an IBD, CD, UC and/or MR-UC patient by administering an anti-TL1A antibody. The kit is an assemblage of materials or components, including at least one of the inventive compositions. Thus, in some embodiments the kit contains a composition including anti-TL1A antibodies, for the treatment of IBD, CD, UC and/or MR-UC, as described above. In other embodiments, the kits contains all of the components necessary and/or sufficient to perform a detection assay for TL1A, including all controls, directions for performing assays, and any necessary software for analysis and presentation of results.

The exact nature of the components configured in the inventive kit depends on its intended purpose. For example, some embodiments are configured for the purpose of treating IBD, CD, UC and/or MR-UC. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat or alleviate IBD, CD, UC and/or MR-UC. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment.

The packaging materials employed in the kit are those customarily utilized in gene expression assays and in the administration of treatments. As used herein, the term "package" refers to a suitable solid matrix or material such as glass, plastic, paper, foil, and the like, capable of holding the individual kit components. Thus, for example, a package can be a glass vial or prefilled syringes used to contain suitable quantities of an inventive composition containing anti-TL1A antibodies and/or primers and probes for TL1A. The packaging material generally has an external label which indicates the contents and/or purpose of the kit and/or its components.

EXAMPLES

The following examples are illustrative of the embodiments described herein and are not to be interpreted as limiting the scope of the described embodiments. To the extent that specific materials are mentioned, it is merely for purposes of illustration and is not intended to be limiting. One skilled in the art may develop equivalent means or reactants without the exercise of inventive capacity and without departing from the scope of this disclosure.

Example 1

Generation of Immunogen and Immunization Protocol for Hybridoma Generation

A recombinant TL1A protein having a point mutation C66S (as counted from the leading methionine in the full length protein) and lacking the leading 57 amino acids was expressed in *E. coli*. The recombinant TL1A sequence is represented by SEQ ID NO: 33

(QLRAQGEASVQFQALKGQEFAPSHQQVYAPLRADGDKPRAHLTVVRQTP

TQHFKNQFPALHWEHELGLAFTKNRMNYTNKFLLIPESGDYFIYSQVTFR

GMTSECSEIRQAGRPNKPDSITVVITKVTDSYPEPTQLLMGTKSVCEVGS

NWFQPIYLGAMFSLQEGDKLMVNVSDISLVDYTKEDKTFFGAFLL).

A TL1A expressing HEK293 cell line was generated by transduction with a lenti viral construct containing the sequence for the full length TL1A protein. This cell line expresses both the membrane bound and secreted forms of the protein (as confirmed by flow cytometry and ELISA based methods respectively). The sequence of TL1A expressed by the HEK293 Cell Line is represented by SEQ ID NO: 34

(MAEDLGLSFGETASVEMLPEHGSCRPKARSSSARWALTCCLVLLPFLAG

LTTYLLVSQLRAQGEACVQFQALKGQEFAPSHQQVYAPLRADGDKPRAHL

TVVRQTPTQHFKNQFPALHWEHELGLAFTKNRMNYTNKFLLIPESGDYFI

YSQVTFRGMTSECSEIRQAGRPNKPDSITVVITKVTDSYPEPTQLLMGTK

SVCEVGSNWFQPIYLGAMFSLQEGDKLMVNVSDISLVDYTKEDKTFFGAF

LL).

Mice were immunized with multiple rounds of immunization using both the recombinant protein and the TL1A expressing cell line. The strategy involved a primary immunization and two rounds of boosters. Two groups of animals were immunized, swapping the primary and booster immunogens between the groups: group 1: primary immunization with recombinant TL1A protein and boost with TL1A expressing cell line; and group 2: primary immunization with TL1A expressing cell line and boost with recombinant TL1A protein. B cells removed from the mice were fused with myeloma cells to generate hybridomas expressing 5C3D11 and 9E12E5 antibodies.

Monoclonal Antibody Sequencing of Hybridoma 5C3D11

Total RNA was extracted from frozen hybridoma cells and cDNA was synthesized from the RNA. PCR was then performed to amplify the variable regions (heavy and light chains) of the antibody, which were then cloned into a standard cloning vector separately and sequenced.

Materials and Methods

Materials used include hybridoma cells, TRIzol® Reagent (Ambion, Cat. No. 15596-026), and PrimeScript™ 1st Strand cDNA Synthesis Kit (Takara, Cat. No. 6110A).

Total RNA Extraction and Reverse Transcription Polymerase Chain Reaction (RT-PCR)

Total RNA was isolated from the hybridoma cells following the technical manual of TRIzol® Reagent. The total RNA was analyzed by agarose gel electrophoresis.

Total RNA was reverse transcribed into cDNA using isotype-specific anti-sense primers or universal primers following the technical manual of PrimeScript™ 1st Strand cDNA Synthesis Kit. The antibody fragments of VH and VL were amplified according to the standard operating procedure of RACE of GenScript.

Cloning of Antibody Gene, Screening and Sequencing

Amplified antibody fragments were separately cloned into a standard cloning vector using standard molecular cloning procedures.

Colony PCR screening was performed to identify clones with inserts of correct sizes. No less than five single colonies with inserts of correct sizes were sequenced for each antibody fragment.

Results and Analysis

The isolated total RNA of the sample was run alongside a DNA marker, Marker III (TIANGEN, Cat. No. MD103) on a 1.5% agarose/GelRed™ gel, as shown in FIG. 1.

Figure 2:
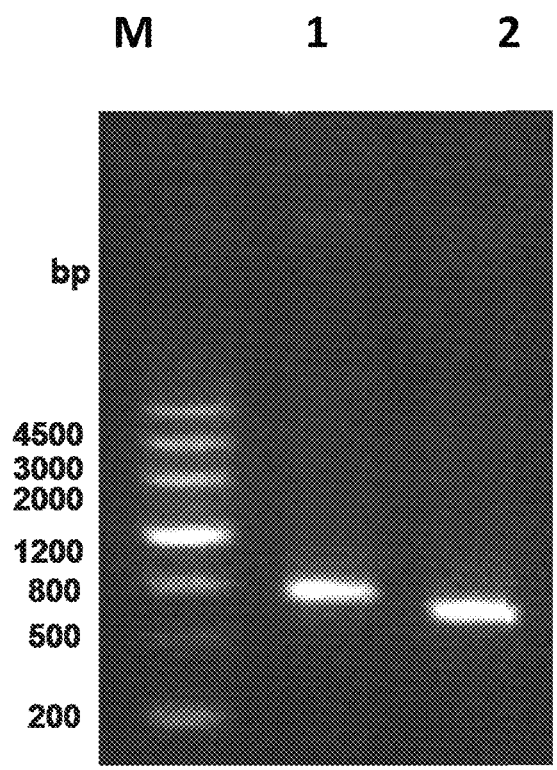
FIG. 2 depicts agarose gel electrophoresis of PCR products of 684842-3. DNA marker, Marker III, is shown in Lane M, the variable heavy chain (VH) of 684842-3 is shown in Lane 1, and the variable light chain (VL) of 684842-3 is shown in Lane 2.

Four microliters of PCR products of each sample were run alongside the DNA marker Marker III on a 1.5% agarose/GelRed™ gel, as shown in FIG. 2. The PCR products were purified and stored at −20° C. until further use.

Sequencing Results and Analysis

Five single colonies with correct VH and VL insert sizes were sent for sequencing. The VH and VL genes of five different clones were found nearly identical. The DNA and amino acid sequences for the heavy chains, light chains and CDR regions are depicted in SEQ ID NOs: 1-16 (see Table 2), which correspond to anti-TL1A antibody 5C3D11.

TABLE 2

Nucleotide and Amino Acid sequences for 5C3D11

| Antibody | Type | Sequence Size | Leader Sequence | Sequence | SEQ ID No: |
|---|---|---|---|---|---|
| | | | | 5C3D11 | |
| Heavy Chain | DNA | 405 bp | FR1-CDR1-<br>FR2-CDR2-<br>FR3-CDR3-<br>FR4 | ATGAAATGCAGCTGGGTTATCTTCTTCCTGATGGCAGT<br>GGTTACAGGGGTCAATTCAGAGGTTCAGCTGCAGCAGT<br>CTGGGGCAGAACTTGTGAAGCCAGGGGCCTCAGTCAAG<br>TTGTCCTGCACAGCTTCTGGCTTCGACATTCAAGACAC<br>CTATATGCACTGGGTGAAGCAGAGGCCTGAACAGGGCC<br>TGGAGTGGATTGGAAGGATTGATCCTGCGAGTGGACAT<br>ACTAAATATGACCCGAAGTTCCAGGTCAAGGCCACTAT<br>AACAACGGACACATCCTCCAACACAGCCTACCTGCAGC<br>TCAGCAGCCTGACATCTGAGGACACTGCCGTCTATTAC<br>TGTTCTAGATCGGGGGGCCTACCTGATGTCTGGGGCGC<br>AGGGACCACGGTCACCGTCTCCTCA | 1 |
| | | | CDR1 | GACACCTATATGCAC | 2 |
| | | | CDR2 | AGGATTGATCCTGCGAGTGGACATACTAAATATGACCC<br>GAAGTTCCAGGTC | 3 |
| | | | CDR3 | TCGGGGGGCCTACCTGATGTC | 4 |
| Heavy Chain | Amino Acid | 135 AA | FR1-CDR1-<br>FR2-CDR2-<br>FR3-CDR3-<br>FR4 | MKCSWVIFFLMAVVTGVNS*EVQLQQSGAELVKPGASVK*<br>*LSCTASGFDIQ*DTYMH*WVKQRPEQGLEWIG*RIDPASGH*<br>TKYDPKFQV*KATITTDTSSNTAYLQLSSLTSEDTAVYY*<br>*C*SRSGGLPDV*WGAGTTVTVSS* | 5 |
| | | | CDR1 | DTYMH | 6 |
| | | | CDR2 | RIDPASGHTKYDPKFQV | 7 |
| | | | CDR3 | SGGLPDV | 8 |
| Light Chain | DNA | 384 bp | FR1-CDR1-<br>FR2-CDR2-<br>FR3-CDR3-<br>FR4 | ATGGATTTTCAAGTGCAGATTTTAGCTTCCTGCTAATC<br>AGTGCTTCAGTCATAATGTCCAGAGGACAAATTGTTCT<br>CTCCCAGTCTCCTGCAATCCTGTCTGCATCTCCAGGGG<br>AGAAGGTCACAATGACTTGCAGGGCCAGCTCAAGTGTA<br>AGTTACATGTACTGGTACCAGCAGAAGCCTGGATCCTC<br>CCCCAAACCCTGGATTTATGCCACATCCAACCTGGCTT<br>CTGGAGTCCCTGATCGCTTCAGTGGCAGTGGGTCTGGG<br>ACCTCTTACTCTCTCACAATCAGCAGAGTGGAGGCTGA<br>AGATGCTGCCACTTATTACTGCCAGCAGTGGAGTGGTA<br>ACCCACGGACGTTCGGTGGAGGCACCAAGCTGGAAATC<br>AAA | 9 |

TABLE 2-continued

Nucleotide and Amino Acid sequences for 5C3D11

| Antibody | Sequence Type | Size | Leader Sequence | Sequence | SEQ ID No: |
|---|---|---|---|---|---|
| | | | CDR1 | AGGGCCAGCTCAAGTGTAAGTTACATGTAC | 10 |
| | | | CDR2 | GCCACATCCAACCTGGCTTCT | 11 |
| | | | CDR3 | CAGCAGTGGAGTGGTAACCCACGGACG | 12 |
| Light Chain | Amino Acid | 128 AA | FR1-CDR1-<br>FR2-CDR2-<br>FR3-CDR3-<br>FR4 | MDFQVQIFSFLLISASVIMSRGQIVLSQSPAILSASPG<br>EKVTMTCRASSSVSYMYWYQQKPGSSPKPWIYATSNLA<br>SGVPDRFSGSGSGTSYSLTISRVEAEDAATYYCQQWSG<br>NPRTFGGGTKLEIK | 13 |
| | | | CDR1 | RASSSVSYMY | 14 |
| | | | CDR2 | ATSNLAS | 15 |
| | | | CDR3 | QQWSGNPRT | 16 | nt-nucleotide; aa-amino acid

Monoclonal Antibody Sequencing of Hybridoma 9E12E5

Total RNA was extracted from frozen hybridoma cells and cDNA was synthesized from the RNA. PCR was then performed to amplify the variable regions (heavy and light chains) of the antibody, which were then cloned into a standard cloning vector separately and sequenced.

Materials and Methods

Materials used include hybridoma cells; TRIzol® Reagent (Ambion, Cat. No. 15596-026); and PrimeScript™ 1st Strand cDNA Synthesis Kit (Takara, Cat. No. 6110A).

Total RNA Extraction and Reverse Transcription Polymerase Chain Reaction (RT-PCR)

Total RNA was isolated from the hybridoma cells following the technical manual of TRIzol® Reagent. The total RNA was analyzed by agarose gel electrophoresis.

Total RNA was reverse transcribed into cDNA using isotype-specific anti-sense primers or universal primers following the technical manual of PrimeScript™ 1st Strand cDNA Synthesis Kit. The antibody fragments of VH and VL were amplified according to the standard operating procedure of RACE of GenScript.

Cloning of Antibody Genes, Screening and Sequencing

Amplified antibody fragments were separately cloned into a standard cloning vector using standard molecular cloning procedures.

Colony PCR screening was performed to identify clones with inserts of correct sizes. No less than five single colonies with inserts of correct sizes were sequenced for each antibody fragment.

Results and Analysis

Figure 3:
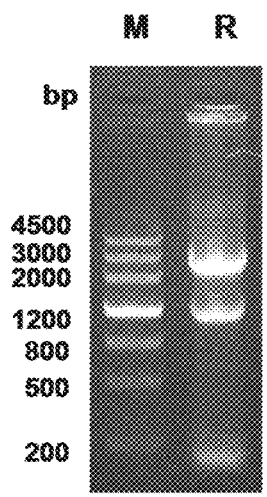
FIG. 3 depicts an agarose gel electrophoresis of total RNA from hybridoma 684842-6 (9E12E5). DNA marker, Marker III, is shown in Lame M and Total RNA of 684842-6 is shown in Lane R.

The isolated total RNA of the sample was run alongside a DNA marker Marker III (TIANGEN, Cat. No. MD103) on a 1.5% agarose/GelRed™ gel, as shown in FIG. 3.

Figure 4:
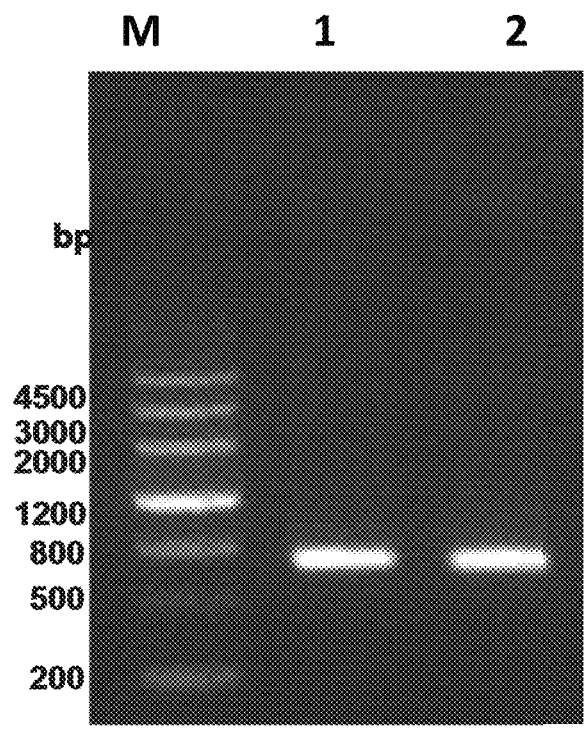
FIG. 4 depicts an agarose gel electrophoresis of PCR products of 684842-6. DNA marker, Marker III, is shown in Lane M, the VH of 684842-6 is shown in Lane 1, and the VL of 684842-6 is shown in Lane 2.

Four microliters of PCR products of each sample were run alongside the DNA marker Marker III on a 1.5% agarose/GelRed™ gel, as shown in FIG. 4. The PCR products were purified and stored at −20° C. until further use.

Sequencing Results and Analysis

Five single colonies with correct VH and VL insert sizes were sent for sequencing. The VH and VL genes of five different clones were found nearly identical. The DNA and amino acid sequences for the heavy chains, light chains and CDR regions are depicted in SEQ ID NOs: 17-32 (see Table 3), which correspond to anti-TL1A antibody 9E12E5.

TABLE 3

Nucleotide and Amino Acid sequences for 9E12E5

| Antibody | Sequence Type | Size | Leader Sequence | Sequence | SEQ ID No: |
|---|---|---|---|---|---|
| | | | | 9E12E5 | |
| Heavy Chain | DNA | 405 bp | FR1-CDR1-<br>FR2-CDR2-<br>FR3-CDR3-<br>FR4 | ATGGGATGGAGCTGGGTCTTTCTCTTCCTCCTGTCAGTGACT<br>GCAGGTGTCCACTCC*CAGGTTCACCTGCAGCAGTCTGGACCT*<br>*GAACTGGTAAAGCCTGGGGCTTCAGTGAAGTTGTCCTGCAAG*<br>*GCTTCTGGCTACACCTTCACA*AAGTATGATATAAAC*TGGGTG*<br>*AGGCAGAGGCCTGAACAGGGACTTGAGTGGATTGGA*TGGATT<br>TTTCCTGGAGATGGTAGAACTGACTACAATGAGAAGTTCAAG<br>GGT*AAGGCCACACTGACTACAGACAAATCCTCCAGCACAGCC*<br>*TACATGGAGGTCAGCAGGCTGACATCTGAGGACTCTGCTGTC*<br>*TATTTCTGTGCAAGA*TATGGCCCCGCTATGGACTAC*TGGGGT*<br>*CAAGGAACCTCAGTCACCGTCGCCTCA* | 17 |

TABLE 3-continued

Nucleotide and Amino Acid sequences for 9E12E5

| Antibody | Sequence Type | Size | Leader Sequence | Sequence | SEQ ID No: |
|---|---|---|---|---|---|
| | | | CDR1 | AAGTATGATATAAAC | 18 |
| | | | CDR2 | TGGATTTTTCCTGGAGATGGTAGAACTGACTACAATGAGAAG TTCAAGGGT | 19 |
| | | | CDR3 | TATGGCCCCGCTATGGACTA | 20 |
| Heavy Chain | Amino Acid | 135 AA | FR1-CDR1- FR2-CDR2- FR3-CDR3- FR4 | MGWSWVFLFLLSVTAGVHS*QVHLQQSGPELVKPGASVKLSCK ASGYTFTKYDINWVRQRPEQGLEWIGWIFPGDGRTDYNEKFK GKATLTTDKSSSTAYMEVSRLTSEDSAVYFCARYGPAMDYWG QGTSVTVAS* | 21 |
| | | | CDR1 | KYDIN | 22 |
| | | | CDR2 | WIFPGDGRTDYNEKFKG | 23 |
| | | | CDR3 | YGPAMDY | 24 |
| Light Chain | DNA | 393 bp | FR1-CDR1- FR2-CDR2- FR3-CDR3- FR4 | ATGAAGTTGCCTGTTAGGCTGTTGGTGCTGATGTTCTGGATT CCTGCTTCCAGCAGTGATGTTTTGATGACCCAAACTCCACTC TCCCTGCCTGTCAGTCTTGGAGATCAAGCCTCCATCTCTTGC AGATCTAGTCAGACCATTGTACATAGTAATGGAGACACCTAT TTAGACTGGTTCCTGCAGAAACCAGGCCAGTCTCCAAAGCTC CTGATCTACAAAGTTTCCAACCGATTTTCTGGGGTCCCAGAC AGGTTCAGTGGCAGTGGATCAGGGACAGATTTCACACTCAAG ATCAGCAGAGTGGAGGCTGAGGATCTGGGAGTTTATTACTGC TTTCAAGGTTCACATGTTCCGTACACGTTCGGAGGGGGGACC AAGCTGGAAATAAAA | 25 |
| | | | CDR1 | AGATCTAGTCAGACCATTGTACATAGTAATGGAGACACCTAT TTAGAC | 26 |
| | | | CDR2 | AAAGTTTCCAACCGATTTTCT | 27 |
| | | | CDR3 | TTTCAAGGTTCACATGTTCCGTACACG | 28 |
| Light Chain | Amino Acid | 131 AA | FR1-CDR1- FR2-CDR2- FR3-CDR3- FR4 | MKLPVRLLVLMFWIPASSSDVLMTQTPLSLPVSLGDQASISC RSSQTIVHSNGDTYLDWFLQKPGQSPKLLIYKVSNRFSGVPD RFSGSGSGTDFTLKISRVEAEDLGVYYCFQGSHVPYTFGGGT KLEIK | 29 |
| | | | CDR1 | RSSQTIVHSNGDTYLD | 30 |
| | | | CDR2 | KVSNRFS | 31 |
| | | | CDR3 | FQGSHVPYT | 32 | nt-nucleotide; aa-amino acid

Example 2

Alignment comparison of the two antibody sequences using BLASTP 2.2.32+ for the heavy chain variable region (Table 4) and the light chain variable region (Table 5).

TABLE 4

BLAST Analysis of the Heavy Chain Variable Region

```
Leader sequence-FR1-CDR1-FR2-CDR2-FR3-CDR3-FR4
(SEQ ID NOS 46-47 disclosed, respectively, in order of appearance)
Query 1 = 9E12E5
Subject = 5C3D11
Length = 135
Score = 173 bits (439), Expect = 1e-60, Method: Compositional matrix adjust.
Identities = 84/135 (62%), Positives = 104/135 (77%), Gaps = 0/135 (0%)

Query     1 MGWSWVFLFLLSVTAGVHSQVHLQQSGPELVKPGASVKLSCKASGYTFTKYDINWVRQRP    60
            M  SWV FL++V  GV+S+V LQQSG ELVKPGASVKLSC ASG+     ++WV+QRP
Sbjct     1 MKCSWVIFFLMAVVTGVNSEVQLQQSGAELVKPGASVKLSCTASGEDIQDTYMHWVKQRP    60
```

TABLE 4-continued

BLAST Analysis of the Heavy Chain Variable Region

```
Query    61  EQGLEWIGWIFPGDGRTDYNEKFKGKATLTTDKSSSTAYMEVSRLTSEDSAVYFCARYGP   120
             EQGLEWIG I P  G T Y+ KF+ KAT+TTD SS+TAY+++S LTSED+AVY+C+R G
Sbjct    61  EQGLEWIGRIDPASGHTKYDPKFQVKATITTDTSSNTAYLQLSSLTSEDTAVYYCSRSGG   120

Query   121  AMDYWGQGTSVTVAS                                               135
             D WG GT+VTV+S
Sbjct   121  LPDVWGAGTTVTVSS                                               135
```

TABLE 5

BLAST Analysis of the Light Chain Variable Region

```
Leader sequence-FR1-CDR1-FR2-CDR2-FR3-CDR3-FR4
(SEQ ID NOS 48-49 disclosed, respectively, in order of appearance)
Query 1 = 9E12E5
Subject = 5C3D11
Length = 128
Score = 107 bits (268), Expect = 4e-35, Method: Compositional matrix adjust.
Identities = 62/115 (54%), Positives = 80/115 (70%), Gaps = 6/115 (5%)

Query    17  SSSDVLMTQTPLSLPVSLGDQASISCRSSQTIVHSNGDTYLDWFLQKPGQSPKLLIYKVS    76
             S    ++++Q+P  L  S G++ +++CR+S ++      +Y+ W+ QKPG SPK  IY  S
Sbjct    20  SRGQIVLSQSPAILSASPGEKVTMTCRASSSV------SYMYWYQQKPGSSPKPWIYATS    73

Query    77  NRFSGVPDRFSGSGSGTDFTLKISRVEAEDLGVYYCFQGSHVPYTFGGGTKLEIK       131
             N   SGVPDRFSGSGSGT ++L ISRVEAED   YYC Q S  P TFGGGTKLEIK
Sbjct    74  NLASGVPDRFSGSGSGTSYSLTISRVEAEDAATYYCQQWSGNPRTFGGGTKLEIK       128
```

Example 3

Figure 5:
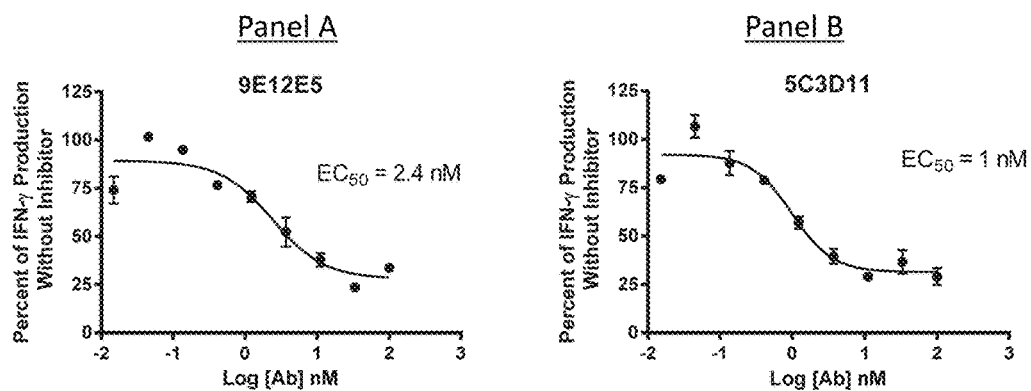
FIG. 5 demonstrates the inhibition of human TL1A induced IFN-γ production by 9E12E5 (panel A) and 5C3D11 (panel B).
Figure 6:
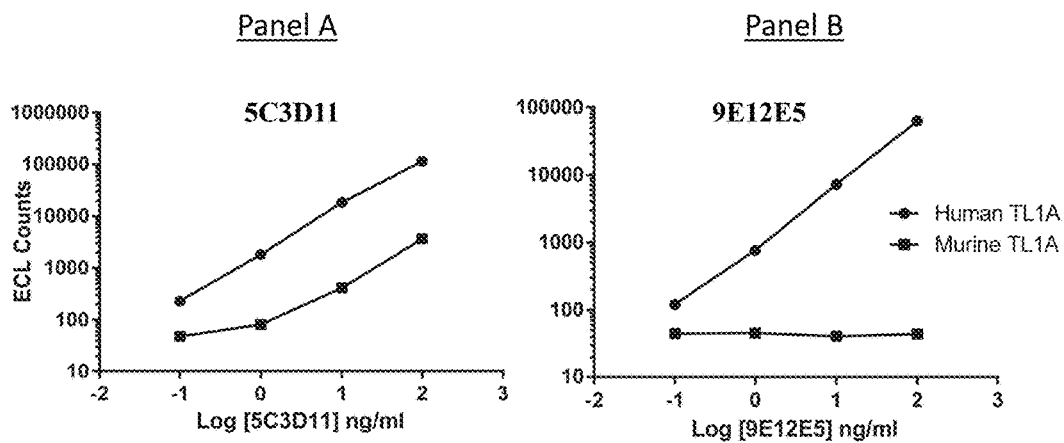
FIG. 6 demonstrates the recognition capability of 5C3D11 (panel A) and 9E12E5 (panel B), to murine TL1A.
Figure 7:
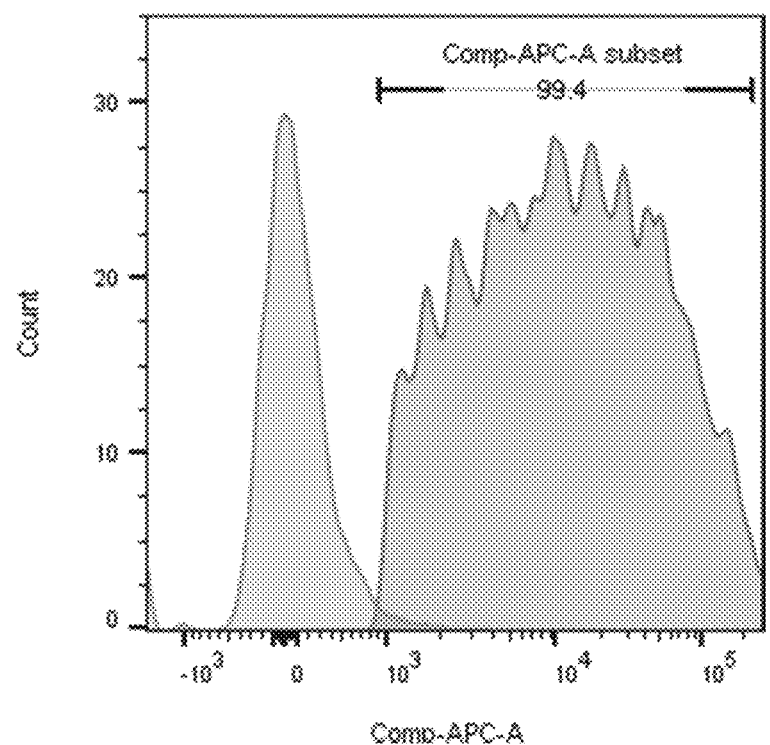
FIG. 7 depicts histogram graphs showing the fluorescent staining of 5C3D11 (panel A) and 9E12E5 (panel B) anti-TL1A antibodies on the TL1A expressing HEK293 cell line compared to the untransfected HEK293 cell line.
Figure 7:
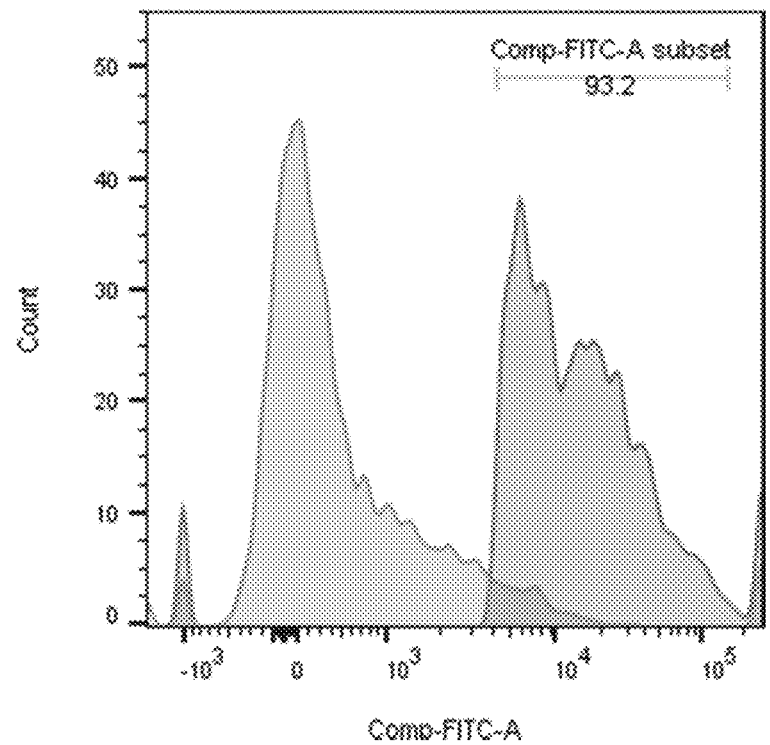

Anti-human TL1A monoclonal antibodies 9E12E5 and 5C3D11 neutralize the activity of human TL1A in vitro. The effect of the TL1A antibodies on IFN-γ production was assessed and both TL1A antibodies demonstrate an inhibition of TL1A induced IFN-γ production, as shown in FIG. 5. MSD plates were coated with murine TL1A and incubated with various concentrations of 5C3D11 or 9E12E5 to evaluate the ability of the antibody to recognize murine TL1A, as shown in FIG. 6. Human TL1A was included as a positive control. 5C3D11 recognizes murine TL1A in a concentration dependent manner. The binding profile of both the 5C3D11 and 9E12E5 antibodies were assessed using a TL1A transfected HEK293 cell line and compared to the untransfected parental HEK293 cell line. Fluorescent staining of the anti-TL1A antibodies in TL1A expressing HEK293 cells is compared to the untransfected parental HEK293 cells, as shown in FIG. 7. The binding affinity for the anti-TL1A antibodies was measured by Biacore, with the dissociation constants shown in Table 6.

TABLE 6

Binding Affinity Values for anti-TL1A Antibodies

| Antibody | Analyte | $K_D$ (M) |
| --- | --- | --- |
| 5C3D11 | TL1A | 7.90E-11 |
| 9E12E5 | TL1A | 5.20E-10 |

Example 4

The efficacy of anti-TL1A antibodies in animal models of colitis is performed.

Anti-TL1A antibodies are tested in rodent models of acute colitis induced by intrarectal administration of di- or tri-nitrobenzenesulfonic acid (D/TNBS) or oxazolone, and chronic colitis induced by administration of DSS in drinking water or transfer of CD45RB$^{hi}$ T cells. DNBS and oxazolone induce localized ulceration and inflammation. DSS administration induces robust generalized inflammation of the intestinal tract characterized by erosive lesions and inflammatory infiltrate. Symptoms of all these models usually include diarrhea, occult blood, weight loss and occasionally rectal prolapse.

In a prophylactic model, antibody treatment begins at the start of administration of the colitis-inducing compound. In a therapeutic model, antibody treatment begins several days after commencement of induction. The effect of the treatment on weight, stool consistency and occult blood, as well as microscopic effects on epithelial integrity and degree of inflammatory infiltrate is determined. Daily clinical scoring is performed based on stool consistency and presence of occult blood giving a disease activity index (DAI) score.

Example 5

A phase 1 clinical trial is performed to evaluate the safety, tolerability, pharmacokinetics and pharmacodynamics of an anti-TL1A antibody provided herein in subjects having Crohn's Disease.

Single ascending dose (SAD) arms: Subjects in each group (subjects are grouped based on the presence or absence of a risk variant) receive either a single dose of the antibody or a placebo. Exemplary doses are 1, 3, 10, 30, 100, 300, 600 and 800 mg of antibody. Safety monitoring and PK assessments are performed for a predetermined time. Based on evaluation of the PK data, and if the antibody is deemed to be well tolerated, dose escalation occurs, either within the same groups or a further group of healthy subjects. Dose escalation continues until the maximum dose has been attained unless predefined maximum exposure is reached or intolerable side effects become apparent.

Multiple ascending dose (MAD) arms: Subjects in each group (subjects are grouped based on the presence or absence of a risk variant) receive multiple doses of the antibody or a placebo. The dose levels and dosing intervals are selected as those that are predicted to be safe from the SAD data. Dose levels and dosing frequency are chosen to achieve therapeutic drug levels within the systemic circulation that are maintained at steady state for several days to allow appropriate safety parameters to be monitored. Samples are collected and analyzed to determination PK profiles.

Inclusion Criteria: Healthy subjects of non-childbearing potential between the ages of 18 and 55 years. Healthy is defined as no clinically relevant abnormalities identified by a detailed medical history, full physical examination, including blood pressure and pulse rate measurement, 12 lead ECG and clinical laboratory tests. Female subjects of non-childbearing potential must meet at least one of the following criteria: (1) achieved postmenopausal status, defined as: cessation of regular menses for at least 12 consecutive months with no alternative pathological or physiological cause; and have a serum follicle stimulating hormone (FSH) level within the laboratory's reference range for postmenopausal females; (2) have undergone a documented hysterectomy and/or bilateral oophorectomy; (3) have medically confirmed ovarian failure. All other female subjects (including females with tubal ligations and females that do NOT have a documented hysterectomy, bilateral oophorectomy and/or ovarian failure) will be considered to be of child-bearing potential. Body Mass Index (BMI) of 17.5 to 30.5 kg/m2; and a total body weight >50 kg (110 lbs). Evidence of a personally signed and dated informed consent document indicating that the subject (or a legal representative) has been informed of all pertinent aspects of the study.

Two groups of healthy subjects are selected: subjects having a risk variant whose presence is associated with an increase in susceptibility to Crohn's Disease, and subjects lacking the risk variant.

Exclusion Criteria: Evidence or history of clinically significant hematological, renal, endocrine, pulmonary, gastrointestinal, cardiovascular, hepatic, psychiatric, neurologic, or allergic disease (including drug allergies, but excluding untreated, asymptomatic, seasonal allergies at time of dosing). Subjects with a history of or current positive results for any of the following serological tests: Hepatitis B surface antigen (HBsAg), Hepatitis B core antibody (HBcAb), anti-Hepatitis C antibody (HCV Ab) or human immunodeficiency virus (HIV). Subjects with a history of allergic or anaphylactic reaction to a therapeutic drug. Treatment with an investigational drug within 30 days (or as determined by the local requirement, whichever is longer) or 5 half-lives or 180 days for biologics preceding the first dose of study medication. Pregnant females; breastfeeding females; and females of childbearing potential.

Primary Outcome Measures: Incidence of dose limiting or intolerability treatment related adverse events (AEs) [Time Frame: 12 weeks]. Incidence, severity and causal relationship of treatment emergent AEs (TEAEs) and withdrawals due to treatment emergent adverse events [Time Frame: 12 weeks]. Incidence and magnitude of abnormal laboratory findings [Time Frame: 12 weeks]. Abnormal and clinically relevant changes in vital signs, blood pressure (BP) and electrocardiogram (ECG) parameters [Time Frame: 12 weeks].

Secondary Outcome Measures:

Single Ascending Dose: Maximum Observed Plasma Concentration (Cmax) [Time Frame: 12 weeks]. Single Ascending Dose: Time to Reach Maximum Observed Plasma Concentration (Tmax) [Time Frame: 12 weeks]. Single Ascending Dose: Area under the plasma concentration-time profile from time zero to 14 days (AUC14 days) [Time Frame: 12 weeks]. Single Ascending Dose: Area under the plasma concentration-time profile from time zero extrapolated to infinite time (AUCinf) [Time Frame: 12 weeks]. Single Ascending Dose: Area under the plasma concentration-time profile from time zero to the time of last quantifiable concentration (AUClast) [Time Frame: 12 weeks]. Single Ascending Dose: Dose normalized maximum plasma concentration (Cmax[dn]) [Time Frame: 12 weeks]. Single Ascending Dose: Dose normalized area under the plasma concentration-time profile from time zero extrapolated to infinite time (AUCinf[dn]) [Time Frame: 12 weeks]. Single Ascending Dose: Dose normalized area under the plasma concentration-time profile from time zero to the time of last quantifiable concentration (AUClast[dn]) [Time Frame: 12 weeks]. Single Ascending Dose: Plasma Decay Half-Life (t½) [Time Frame: 12 weeks]. Plasma decay half-life is the time measured for the plasma concentration to decrease by one half. Single Ascending Dose: Mean residence time (MRT) [Time Frame: 12 weeks]. Single Ascending Dose: Volume of Distribution at Steady State (Vss) [Time Frame: 6 weeks]. Volume of distribution is defined as the theoretical volume in which the total amount of drug would need to be uniformly distributed to produce the desired blood concentration of a drug. Steady state volume of distribution (Vss) is the apparent volume of distribution at steady-state. Single Ascending Dose: Systemic Clearance (CL) [Time Frame: 6]. CL is a quantitative measure of the rate at which a drug substance is removed from the body.

Multiple Ascending Dose First Dose: Maximum Observed Plasma Concentration (Cmax) [Time Frame: 12 weeks]. Multiple Ascending Dose First Dose: Time to Reach Maximum Observed Plasma Concentration (Tmax) [Time Frame: 12 weeks]. Multiple Ascending Dose First Dose: Area under the plasma concentration-time profile from time zero to time τ, the dosing interval where τ=2 weeks (AUCτ) [Time Frame: 12 weeks]. Multiple Ascending Dose First Dose: Dose normalized maximum plasma concentration (Cmax[dn]) [Time Frame: 12 weeks]. Multiple Ascending Dose First Dose: Dose normalized Area under the plasma concentration-time profile from time zero to time τ, the dosing interval where τ=2 weeks (AUCτ[dn]) [Time Frame: 12 weeks]. Plasma Decay Half-Life (t½) [Time Frame: 12 weeks]. Plasma decay half-life is the time measured for the plasma concentration to decrease by one half. Multiple Ascending Dose First Dose: Mean residence time (MRT) [Time Frame: 12 weeks]. Apparent Volume of Distribution (Vz/F) [Time Frame: 12 weeks]. Volume of distribution is defined as the theoretical volume in which the total amount of drug would need to be uniformly distributed to produce the desired plasma concentration of a drug. Apparent volume of distribution after oral dose (Vz/F) is influenced by the fraction absorbed. Multiple Ascending Dose First Dose: Volume of Distribution at Steady State (Vss) [Time Frame: 12 weeks]. Volume of distribution is defined as the theoretical volume in which the total amount of drug would need to be uniformly distributed to produce the desired blood concentration of a drug. Steady state volume of distribution (Vss) is the apparent volume of distribution at steady-state. Multiple Ascending Dose First Dose: Apparent Oral Clearance (CL/F) [Time Frame: 12 weeks]. Clearance of a drug is a measure of the rate at which a drug is metabolized or eliminated by normal biological processes. Clearance obtained after oral dose (apparent oral clearance) is influenced by the fraction of the dose absorbed. Clearance is estimated from population pharmacokinetic (PK) modeling. Drug clearance is a quantitative measure of the rate at which a drug substance is removed from the blood. Multiple Ascending Dose First Dose: Systemic Clearance (CL) [Time Frame: 12 weeks]. CL is a quantitative measure of the rate at which a drug substance is removed from the body.

Multiple Ascending Dose Multiple Dose: Maximum Observed Plasma Concentration (Cmax) [Time Frame: 12 weeks]. Multiple Ascending Dose Multiple Dose: Time to Reach Maximum Observed Plasma Concentration (Tmax) [Time Frame: 12 weeks]. Multiple Ascending Dose Multiple Dose: Area under the plasma concentration-time profile from time zero to time $\tau$, the dosing interval where $\tau=2$ weeks (AUC$\tau$) [Time Frame: 12 weeks]. Multiple Ascending Dose Multiple Dose: Dose normalized maximum plasma concentration (Cmax[dn]) [Time Frame: 12 weeks]. Multiple Ascending Dose Multiple Dose: Dose normalized Area under the plasma concentration-time profile from time zero to time $\tau$, the dosing interval where $\tau=2$ weeks (AUC$\tau$[dn]) [Time Frame: 12 weeks]. Multiple Ascending Dose Multiple Dose: Plasma Decay Half-Life (t½) [Time Frame: 12 weeks]. Plasma decay half-life is the time measured for the plasma concentration to decrease by one half. Multiple Ascending Dose Multiple Dose: Apparent Volume of Distribution (Vz/F) [Time Frame: 12 weeks]. Volume of distribution is defined as the theoretical volume in which the total amount of drug would need to be uniformly distributed to produce the desired plasma concentration of a drug. Apparent volume of distribution after oral dose (Vz/F) is influenced by the fraction absorbed. Multiple Ascending Dose Multiple Dose: Volume of Distribution at Steady State (Vss) [Time Frame: 12 weeks ]. Volume of distribution is defined as the theoretical volume in which the total amount of drug would need to be uniformly distributed to produce the desired blood concentration of a drug. Steady state volume of distribution (Vss) is the apparent volume of distribution at steady-state. Multiple Ascending Dose Multiple Dose: Apparent Oral Clearance (CL/F) [Time Frame: 12 weeks ]. Clearance of a drug is a measure of the rate at which a drug is metabolized or eliminated by normal biological processes. Clearance obtained after oral dose (apparent oral clearance) is influenced by the fraction of the dose absorbed. Clearance was estimated from population pharmacokinetic (PK) modeling. Drug clearance is a quantitative measure of the rate at which a drug substance is removed from the blood. Multiple Ascending Dose Multiple Dose: Systemic Clearance (CL) [Time Frame: 12 weeks]. CL is a quantitative measure of the rate at which a drug substance is removed from the body. Multiple Ascending Dose Multiple Dose: Minimum Observed Plasma Trough Concentration (Cmin) [Time Frame: 12 weeks]. Multiple Ascending Dose Multiple Dose: Average concentration at steady state (Cav) [Time Frame: 12 weeks]. Multiple Ascending Dose Multiple Dose: Observed accumulation ratio (Rac) [Time Frame: 12 weeks]. Multiple Ascending Dose Multiple Dose: Peak to trough fluctuation (PTF) [Time Frame: 12 weeks]. Multiple Ascending Dose Additional Parameter: estimate of bioavailability (F) for subcutaneous administration at the corresponding intravenous dose [Time Frame: 12 weeks]. Immunogenicity for both Single Ascending Dose and Multiple Ascending Dose: Development of anti-drug antibodies (ADA) [Time Frame: 12 weeks].

Example 6

A phase 1b open label clinical trial is performed to evaluate efficacy of an anti-TL1A antibody provided herein on patients having a risk variant associated with Crohn's Disease.

Arms: 10 patients positive for a risk variant whose presence is associated with an increase in susceptibility to Crohn's Disease are administered the antibody. 5-10 patients negative for the risk variant are administered the antibody. Patients are monitored in real-time. Central ready of endoscopy and biopsy is employed, with readers blinded to point of time of treatment and endpoints.

Inclusion Criteria: Two groups of subjects are selected: subjects having a risk variant whose presence is associated with an increase in susceptibility to Crohn's Disease, and subjects lacking the risk variant.

Primary Outcome Measures: Simple Endoscopic Score for Crohn's Disease (SESCD), Crohn's Disease Activity Index (CDAI), and Patient Reported Outcome (PRO). If risk variant positive group shows 50% reduction from baseline, a Phase 2a clinical trial is performed.

Inclusion Criteria: PRO entry criteria: Abdominal pain score of 2 or more and/or stool frequency score of 4 or more. Primary outcome would be pain core of 0 or 1 and stool frequency score of 3 or less with no worsening from baseline. Endoscopy entry criteria: SESCD ileum only entry at score of 4 and 6 if colon is involved. Primary endoscopic outcome is 40-50% delta of mean SESCD.

Example 7

A phase 2a clinical trial is performed to evaluate the efficacy of an anti-TL1A antibody provided herein in subjects having Crohn's Disease.

Arms: 40 patients per arm (antibody and placebo arms) are treated with antibody or placebo for 12 weeks. An interim analysis is performed after 20 patients from each group are treated at the highest dose to look for a 40-50% delta between placebo and treated group in primary outcome (50% reduction from baseline in SESCD, CDAI, and PRO).

Primary Outcome Measures: Simple Endoscopic Score for Crohn's Disease (SESCD), Crohn's Disease Activity Index (CDAI), and Patient Reported Outcome (PRO).

Inclusion Criteria: PRO entry criteria: Abdominal pain score of 2 or more and/or stool frequency score of 4 or more. Primary outcome would be pain core of 0 or 1 and stool frequency score of 3 or less with no worsening from baseline. Endoscopy entry criteria: SESCD ileum only entry at score of 4 and 6 if colon is involved. Primary endoscopic outcome is 40-50% delta of mean SESCD.

Example 8

Humanized anti-TL1A antibodies were generated. Briefly, a library of antibodies was created comprising the CDRs of 5C3D11 and framework regions from human germline antibodies. The library was screened using phage display to identify antibodies having affinity to human TL1A (hTL1A) antigen. Sixty clones were affinity ranked using surface plasmon resonance (SPR). Five antibodies were selected based on affinity data and evaluation of framework sequence: AS12816, AS12819, AS12823, AS12824, and AS12825. Sequence data for the selected clones is shown in Table 7 (VH) and Table 8 (VL). Affinity data for the five selected clones is shown in Table 9. Four of the five selected clones (AS12816, AS12819, AS12823, and AS12824) were selected for multi-cycle affinity measurement, with corresponding data shown in Table 10.

TABLE 7

Humanized anti-TL1A clones: heavy chain sequences.

| Clone | SEQ ID NO. | Sequence |
|---|---|---|
| AS12824 | 35 | QVQLVQSGAEVKKPGASVKVSCKASGFDICDTYM HWVKQRPGQGLEWIGRIDPASGHTKYDPKFQVRA TITTDTSTSTAYLELSSLRSEDTAVYYCARSGGL PDVWGQGTTVTVSS |
| AS12823 | 36 | QVQLVQSGAEVKKPGASVKLSCKASGFDICDTYM HWVRQRPGQGLEWIGRIDPASGHTKYDPKFQVRA TMTTDTSTSTVYLELSSLRSEDTAVYYCARSGGL PDVWGQGTTVTVSS |
| AS12819 | 37 | QVQLVQSGAEVVKPGASVKLSCKASGFDICDTYM HWVRQRPGQGLEWMGRIDPASGHTKYDPKFQVRV TMTTDTSTSTVYLELSSLRSEDTAVYYCARSGGL PDVWGQGTTVTVSS |
| AS12816 | 38 | QVQLVQSGAEVKKPGASVKVSCKASGFDICDTYM HWVKQRPGQGLEWIGRIDPASGHTKYDPKFQVRA TITRDTSTSTAYLELSSLRSEDTAVYYCSRSGGL PDVWGQGTTVTVSS |
| AS12825 | 39 | QVQLVQSGAEVKKPGASVKVSCKASGFDICDTYM HWVKQAPGQGLEWMGRIDPASGHTKYDPKFQVRA TMTTDTSTSTAYLELSSLRSEDTAVYYCSRSGGL PDVWGQGTTVTVSS |

TABLE 8

Humanized anti-TL1A clones: light chain sequences.

| Clone | SEQ ID NO. | Sequence |
|---|---|---|
| AS12824 | 40 | EIVLTQSPGTLSASPGERATMSCRASSSVSYMYW YQQKPGQAPRPWIYATSNLASGVPDRFSGSGSGT DYTLTISRVEPEDFAVYYCQQWSGNPRTFGGGTK LEIK |
| AS12823 | 41 | EIVLTQSPGTLSLSPGERATMSCRASSSVSYMYW YQQKPGQAPRPWIYATSNLASGIPDRFSGSGSGT DFTLTISRVEPEDFAVYYCQQWSGNPRTFGGGTK LEIK |
| AS12819 | 42 | EIVLTQSPGTLSLSPGERVTMSCRASSSVSYMYW YQQKPGQAPRPWIYATSNLASGVPDRFSGSGSGT DFTLTISRVEPEDFAVYYCQQWSGNPRTFGGGTK VEIK |
| AS12816 | 43 | EIVLTQSPGTLSASPGERVTLSCRASSSVSYMYW YQQKPGQAPRPWIYATSNLASGVPDRFSGSGSGT DFTLTISRLEPEDFAVYYCQQWSGNPRTFGGGTK LEIK |
| AS12825 | 44 | EIVLTQSPGTLSASPGERVTMSCRASSSVSYMYW YQQKPGQAPRLLIYATSNLASGVPDRFSGSGSGT DFTLTISRVEPEDFAVYYCQQWSGNPRTFGGGTK LEIK |

TABLE 9

Humanized anti-TL1A clones: light chain mutations.

| Clone NO. | | Ligand | Curve | ka (1/Ms) | kd (1/s) | KD (M) | Rmax (RU) | Chi2 (RU2) |
|---|---|---|---|---|---|---|---|---|
| | | | | Controls | | | | |
| | | graft-BM-SH | Fc = 2-1 | 1.01E+06 | 6.39E−06 | 6.32E−12 | 445.9 | 1.48 |
| | | graft-BM-SH | Fc = 2-1 | 1.46E+06 | 1.70E−05 | 1.16E−11 | 437.2 | 49.10 |
| | | chimeric | Fc = 4-1 | 1.56E+06 | 3.70E−05 | 2.37E−11 | 247.9 | 44.00 |
| | | chimeric | Fc = 4-1 | 9.03E+05 | 3.12E−05 | 3.46E−11 | 269.9 | 1.00 |
| | | | | Affinity ranked clones | | | | |
| AS12824 | 15 | | Fc = 3-1 | 1.03E+06 | 1.69E−05 | 1.63E−11 | 324 | 1.09 |
| AS12835 | 28 | | Fc = 2-1 | 9.22E+05 | 2.73E−05 | 2.96E−11 | 119.9 | 25.70 |
| AS12823 | 14 | | Fc = 3-1 | 8.64E+05 | 3.66E−05 | 4.24E−11 | 155 | 0.58 |
| AS12819 | 10 | | Fc = 3-1 | 8.25E+05 | 3.81E−05 | 4.62E−11 | 178 | 1.05 |
| AS12831 | 23 | | Fc = 4-1 | 8.25E+05 | 3.83E−05 | 4.64E−11 | 167.4 | 0.33 |
| AS12821 | 12 | | Fc = 3-1 | 1.05E+06 | 4.93E−05 | 4.72E−11 | 342 | 1.11 |
| AS12851 | 54 | | Fc = 4-1 | 8.78E+05 | 4.52E−05 | 5.15E−11 | 185.8 | 0.82 |
| AS12816 | 6 | | Fc = 2-1 | 7.63E+05 | 4.73E−05 | 6.20E−11 | 273.4 | 0.39 |
| AS12850 | 52 | | Fc = 2-1 | 1.37E+06 | 9.21E−05 | 6.71E−11 | 97.5 | 1.71 |
| AS12817 | 7 | | Fc = 2-1 | 1.00E+06 | 6.92E−05 | 6.89E−11 | 93.5 | 0.37 |
| AS12839 | 33 | | Fc = 3-1 | 9.93E+05 | 7.46E−05 | 7.52E−11 | 97.7 | 0.62 |
| AS12837 | 30 | | Fc = 2-1 | 8.80E+05 | 6.64E−05 | 7.55E−11 | 195.4 | 0.41 |
| AS12843 | 38 | | Fc = 3-1 | 9.22E+05 | 7.10E−05 | 7.70E−11 | 113.9 | 0.47 |
| AS12838 | 31 | | Fc = 2-1 | 9.04E+05 | 7.14E−05 | 7.90E−11 | 112.7 | 0.24 |
| AS12828 | 20 | | Fc = 4-1 | 7.31E+05 | 5.80E−05 | 7.94E−11 | 180.6 | 0.48 |
| AS12842 | 37 | | Fc = 3-1 | 1.10E+06 | 9.07E−05 | 8.23E−11 | 244.7 | 2.15 |
| AS12841 | 35 | | Fc = 3-1 | 8.32E+05 | 6.87E−05 | 8.26E−11 | 187.9 | 0.54 |
| AS12822 | 13 | | Fc = 3-1 | 8.95E+05 | 7.46E−05 | 8.33E−11 | 121.8 | 0.82 |
| AS12815 | 4 | | Fc = 3-1 | 8.25E+05 | 6.91E−05 | 8.37E−11 | 197.5 | 0.40 |
| AS12820 | 11 | | Fc = 3-1 | 1.14E+06 | 9.54E−05 | 8.40E−11 | 78.1 | 0.54 |
| AS12833 | 26 | | Fc = 3-1 | 7.22E+05 | 6.66E−05 | 9.22E−11 | 160.9 | 2.91 |
| AS12818 | 8 | | Fc = 2-1 | 8.61E+05 | 8.64E−05 | 1.00E−10 | 142.1 | 0.35 |
| AS12825 | 16 | | Fc = 3-1 | 5.18E+05 | 5.45E−05 | 1.05E−10 | 132.1 | 2.95 |
| AS12848 | 49 | | Fc = 2-1 | 7.95E+05 | 8.47E−05 | 1.06E−10 | 125.7 | 0.74 |

TABLE 9-continued

Humanized anti-TL1A clones: light chain mutations.

| Clone NO. | Ligand | Curve | ka (1/Ms) | kd (1/s) | KD (M) | Rmax (RU) | Chi2 (RU2) |
|---|---|---|---|---|---|---|---|
| AS12813 | 2 | Fc = 2-1 | 7.03E+05 | 8.20E−05 | 1.17E−10 | 136 | 0.36 |
| AS12845 | 41 | Fc = 4-1 | 7.65E+05 | 9.35E−05 | 1.22E−10 | 99 | 0.37 |
| AS12849 | 50 | Fc = 2-1 | 8.97E+05 | 1.18E−04 | 1.32E−10 | 92.3 | 0.69 |
| AS12846 | 42 | Fc = 4-1 | 7.80E+05 | 1.03E−04 | 1.33E−10 | 112.2 | 0.34 |
| AS12847 | 45 | Fc = 4-1 | 8.30E+05 | 1.11E−04 | 1.34E−10 | 197.6 | 1.11 |
| AS12832 | 24 | Fc = 4-1 | 7.31E+05 | 9.90E−05 | 1.36E−10 | 104.6 | 0.29 |
| AS12834 | 27 | Fc = 2-1 | 8.38E+05 | 1.31E−04 | 1.57E−10 | 111.3 | 0.58 |
| AS12830 | 22 | Fc = 4-1 | 4.48E+05 | 7.86E−05 | 1.76E−10 | 282.7 | 1.07 |
| AS12840 | 34 | Fc = 3-1 | 9.04E+05 | 1.62E−04 | 1.79E−10 | 37.6 | 0.45 |
| AS12852 | 56 | Fc = 4-1 | 5.06E+05 | 9.18E−05 | 1.81E−10 | 113.6 | 1.65 |
| AS12836 | 29 | Fc = 2-1 | 8.85E+05 | 1.61E−04 | 1.82E−10 | 120.2 | 1.14 |
| AS12827 | 19 | Fc = 4-1 | 3.15E+05 | 5.83E−05 | 1.85E−10 | 308.3 | 1.45 |
| AS12826 | 18 | Fc = 4-1 | 4.91E+05 | 9.15E−05 | 1.86E−10 | 116.9 | 2.33 |
| AS12814 | 3 | Fc = 2-1 | 4.56E+05 | 9.64E−05 | 2.11E−10 | 102.2 | 2.51 |
| AS12829 | 21 | Fc = 4-1 | 3.48E+05 | 1.48E−04 | 4.24E−10 | 202.9 | 0.54 |
| AS12844 | 39 | Fc = 3-1 | 4.95E+05 | 2.27E−04 | 4.58E−10 | 60.7 | 0.54 |
| AS12853 | 59 | Fc = 3-1 | 5.11E+05 | 3.17E−04 | 6.21E−10 | 104 | 2.26 |
|  | 32 | Fc = 2-1 | 1.01E+06 | 3.26E−05 | 3.24E−11 | 90.6 | 0.983 |
|  | 40 | Fc = 3-1 | 1.08E+06 | 4.27E−05 | 3.97E−11 | 79.2 | 1.06 |
|  | 36 | Fc = 3-1 | 5.46E+05 | 2.63E−05 | 4.82E−11 | 59.1 | 28.1 |
|  | 44 | Fc = 4-1 | 8.64E+05 | 4.19E−05 | 4.85E−11 | 76.6 | 28.1 |
|  | 58 | Fc = 3-1 | 1.12E+06 | 7.72E−05 | 6.91E−11 | 86.6 | 0.616 |
|  | 48 | Fc = 4-1 | 9.86E+05 | 7.46E−05 | 7.56E−11 | 56 | 0.474 |
|  | 57 | Fc = 3-1 | 1.05E+06 | 8.69E−05 | 8.29E−11 | 48.2 | 0.825 |
|  | 60 | Fc = 3-1 | 2.02E+06 | 1.78E−04 | 8.81E−11 | 53.9 | 1.77 |
|  | 25 | Fc = 2-1 | 1.03E+06 | 9.75E−05 | 9.43E−11 | 56.4 | 0.27 |
|  | 47 | Fc = 4-1 | 9.01E+05 | 8.60E−05 | 9.55E−11 | 74.1 | 0.332 |
|  | 17 | Fc = 4-1 | 6.25E+05 | 6.00E−05 | 9.60E−11 | 186.7 | 0.735 |
|  | 53 | Fc = 4-1 | 8.08E+05 | 8.26E−05 | 1.02E−10 | 76.3 | 0.803 |
|  | 43 | Fc = 4-1 | 8.35E+05 | 8.64E−05 | 1.03E−10 | 59.2 | 0.153 |
|  | 5 | Fc = 2-1 | 1.05E+06 | 1.17E−04 | 1.11E−10 | 28.1 | 0.203 |
|  | 46 | Fc = 4-1 | 8.23E+05 | 1.06E−04 | 1.29E−10 | 82.7 | 0.261 |
|  | 9 | Fc = 3-1 | 8.71E+05 | 1.27E−04 | 1.46E−10 | 49.5 | 1.76 |
|  | 55 | Fc = 4-1 | 4.82E+06 | 7.16E−04 | 1.48E−10 | 48.1 | 1.59 |
|  | 51 | Fc = 2-1 | 1.15E+06 | 2.79E−04 | 2.42E−10 | 59.2 | 1.86 |
|  | 1 | Fc = 2-1 | 5.10E+04 | 5.15E−04 | 1.01E−08 | 18.4 | 0.2 |
| Negative controls |
| SASA |  | Fc = 4-1 | 7.84E+03 | 9.25E−07 | 1.18E−10 | 19.7 | 0.755 |
| SASA |  | Fc = 4-1 | 7.84E+03 | 9.25E−07 | 1.18E−10 | 19.7 | 0.755 |
| SASA |  | Fc = 2-1 | 1.52E+04 | 4.71E−06 | 3.10E−10 | 21.7 | 0.7 |
| SASA |  | Fc = 2-1 | 1.52E+04 | 4.71E−06 | 3.10E−10 | 21.7 | 0.7 |
| SASA |  | Fc = 3-1 | 2.70E+04 | 2.81E−05 | 1.04E−09 | 7.4 | 0.783 |

TABLE 10

Multi-cycle affinity measurement of binding between hTL1A and humanized antibodies using SPR.

| Ligand | Analyte | $k_a$ (1/Ms) | $k_d$ (1/s) | $K_D$ (M) | Rmax | Chi$^2$ | U-value |
|---|---|---|---|---|---|---|---|
| AS12816 | TL1A | 8.19E+05 | 2.29E− | 2.79E− | 202.6 | 1.51 | 5 |
| AS12819 | TL1A | 9.46E+05 | 1.37E− | 1.45E− | 164.9 | 1.08 | 9 |
| AS12823 | TL1A | 1.11E+06 | <1.00E− | 9.03E− | 175.4 | 1.34 | 12 |
| AS12824 | TL1A | 1.07E+06 | <1.00E− | 9.39E− | 272.9 | 1.6 | 95 |
| BM-SH | TL1A | 9.61E+05 | 5.03E− | 5.24E− | 201.3 | 2.07 | 3 |
| Chimeric | TL1A | 1.26E+06 | 1.15E− | 9.09E− | 261.6 | 1.02 | 7 |

Example 9

A binding competition assay using surface plasmon resonance (SPR) is performed to evaluate whether a test anti-TL1A antibody binds to the same region on TL1A as any anti-TL1A antibody described herein. In this example, the reference antibody comprises the heavy chain CDRs of SEQ ID NOs: 6-8 and the light chain CDRs of SEQ ID NOs: 14-16.

The reference antibody is directly immobilized via amine coupling onto a carboxymethylated dextran sensor chip surface (CMS) using a Biacore 2000 or 3000 instrument. Recombinant soluble human TL1A or murine TL1A diluted to 10 nM in 8.1 mM $Na_2HPO_4$, 1.47 mM $KF_2PO_4$, pH 7.2, 237 mM NaCl, 2.7 mM KCl, 3.4 mM EDTA and 0.01% tween 20 (PBS-NET) is injected for about 1 minute at a flow rate of 10 Rl/minute to achieve binding levels on the immobilized antibody of at least 100 response units (RU). The reference antibody is then injected at 30 nM for 5 minutes in order to saturate all of the potential binding sites on the TL1A. A repeat injection of the reference antibody is performed to confirm this saturation. Next, the test antibody in PBS-NET or PBS-NET alone as a control is injected at 30 nM for 5 minutes. If the test antibody binds to the TL1A saturated with the first antibody, this indicates that the test antibody binds to a non-competing region on TL1A as compared to the reference antibody. If the test antibody did not bind to the saturated TL1A, this indicates that the two antibodies bind to the same region or compete with binding to TL1A. This strategy may be repeated with the test antibody immobilized and the reference antibody injected after the test antibody was bound with TL1A. Each cycle may be repeated. At the end of each cycle, the immobilized antibody surface is regenerated either by a 30-second pulse of 3M $MgCl_2$ or by 0.1% TFA followed by two consecutive 15-second pulses of PBS-NET. All injections are performed at 25° C. at a collection rate of 10 Hz. All sensorgrams are double referenced by using both a control surface and buffer injections.

Example 10

Another binding competition assay using SPR is performed to evaluate whether a test anti-TL1A antibody binds to the same region on TL1A as any anti-TL1A antibody described herein. In this example, the reference antibody comprises the heavy chain CDRs of SEQ ID NOs: 6-8 and the light chain CDRs of SEQ ID NOs: 14-16.

The reference antibody is immobilized to the SPR chip via amine coupled at three or four different densities across the array. The TL1A protein is injected in an increasing concentration series to estimate kinetic parameters and the appropriate concentration for injections during the competition binning experiment. Once the optimal antigen concentration for the binning experiment is determined, regeneration conditions (typically a brief low pH injection) are evaluated to establish the optimal conditions for regeneration between cycles of the binning assay.

Binning is performed using the Pre-Mix approach, where a moderate concentration of TL1A is injected over the array, either by itself, or pre-complexed to the test antibody at saturating antibody concentrations (e.g., 30-50 µg/mL). The assay may be performed such that the test antibody is immobilized and the reference antibody is pre-complexed to the TL1A. Clones that bind to unique regions from the immobilized antibody provide an increase in signal, while competitive clones will decrease the antigen binding signal. The competition assay is run so that all clones are tested as both ligands and analytes.

Various embodiments are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments known to the applicant at this time of filing the application has been presented and is intended for the purposes of illustration and description. The present description is not intended to be exhaustive nor limited to the precise form disclosed and many modifications and variations are possible in the light of the above teachings. The embodiments described serve to explain principles and practical applications, and to enable others skilled in the art to utilize the various embodiments, optionally with various modifications, as are suited to the particular use contemplated. Therefore, it is intended that the disclosure not be limited to the particular embodiments disclosed.

While particular embodiments have been shown and described, it will be obvious to those skilled in the art that, based upon the teachings herein, changes and modifications may be made without departing from this disclosure and its broader aspects and, therefore, the appended claims are to encompass within their scope all such changes and modifications as are within the true spirit and scope of this disclosure. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

---

What is claimed is:

1. An antibody or antigen-binding fragment that specifically binds to a tumor necrosis factor-like protein 1A (TL1A) polypeptide, wherein said antibody or antigen-binding fragment comprises:
   a) a heavy chain comprising a heavy chain complementarity determining region 1 (HCDR1), a heavy chain complementarity determining region 2 (HCDR2), and a heavy chain complementarity determining region 3 (HCDR3), wherein
      i) the HCDR1 comprises a first amino acid sequence of DTYMH of SEQ ID NO: 6;
      ii) the HCDR2 comprises a second amino acid sequence of PASGH of SEQ ID NO: 7; and
      iii) the HCDR3 comprises a third amino acid sequence of SGGLPD of SEQ ID NO: 8; and
   b) a light chain comprising a light chain complementarity determining region 1 (LCDR1), a light chain complementarity determining region 2 (LCDR2), and a light chain complementarity determining region 3 (LCDR3), wherein
      i) the LCDR1 comprises a fourth amino acid sequence of ASSSVSYMY of SEQ ID NO: 14;
      ii) the LCDR2 comprises a fifth amino acid sequence of ATSNLAS of SEQ ID NO: 15; and
      iii) the LCDR3 comprises a sixth amino acid sequence of GNPRT of SEQ ID NO: 16.

2. The antibody or antigen-binding fragment of claim 1, provided that the antibody or antigen-binding fragment is a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, or a combination thereof.

3. The antibody or antigen-binding fragment of claim 2, provided that the antibody or antigen-binding fragment is a humanized antibody.

4. A composition comprising: the antibody or antigen-binding fragment of claim 1, and a pharmaceutically acceptable carrier.

5. The antibody or antigen-binding fragment of claim 1, provided the antibody or antigen binding fragment is an immunoglobulin G (IgG).

6. The antibody or antigen-binding fragment of claim 5, provided the IgG comprises an IgG1.

7. The antibody or antigen-binding fragment of claim 5, provided the IgG comprises an IgG2.

* * * * *

SEQUENCE LISTING

```
<160> NUMBER OF SEQ ID NOS: 49

<210> SEQ ID NO 1
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgaaatgca gctgggttat cttcttcctg atggcagtgg ttacaggggt caattcagag      60
gttcagctgc agcagtctgg ggcagaactt gtgaagccag gggcctcagt caagttgtcc     120
tgcacagctt ctggcttcga cattcaagac acctatatgc actgggtgaa gcagaggcct     180
gaacagggcc tggagtggat tggaaggatt gatcctgcga gtggacatac taaatatgac     240
ccgaagttcc aggtcaaggc cactataaca acggacacat cctccaacac agcctacctg     300
cagctcagca gcctgacatc tgaggacact gccgtctatt actgttctag atcgggggc      360 ctacctgatg tctggggcgc agggaccacg gtcaccgtct cctca                     405
```

```
<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gacacctata tgcac                                                           15

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aggattgatc ctgcgagtgg acatactaaa tatgacccga agttccaggt c                    51

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 tcgggggggcc tacctgatgt c                                                   21

<210> SEQ ID NO 5
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asp Ile
        35                  40                  45

Gln Asp Thr Tyr Met His Trp Val Lys Gln Arg Pro Glu Gln Gly Leu
    50                  55                  60

Glu Trp Ile Gly Arg Ile Asp Pro Ala Ser Gly His Thr Lys Tyr Asp
65                  70                  75                  80

Pro Lys Phe Gln Val Lys Ala Thr Ile Thr Thr Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ser Arg Ser Gly Gly Leu Pro Asp Val Trp Gly Ala Gly
        115                 120                 125

Thr Thr Val Thr Val Ser Ser
    130                 135
```

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Asp Thr Tyr Met His
1               5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Arg Ile Asp Pro Ala Ser Gly His Thr Lys Tyr Asp Pro Lys Phe Gln
1               5                   10                  15

Val

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Ser Gly Gly Leu Pro Asp Val
1               5

<210> SEQ ID NO 9
<211> LENGTH: 384
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
atggattttc aagtgcagat tttcagcttc ctgctaatca gtgcttcagt cataatgtcc      60
agaggacaaa ttgttctctc ccagtctcct gcaatcctgt ctgcatctcc aggggagaag     120
gtcacaatga cttgcagggc cagctcaagt gtaagttaca tgtactggta ccagcagaag     180
cctggatcct cccccaaacc ctggatttat gccacatcca acctggcttc tggagtccct     240
gatcgcttca gtggcagtgg gtctgggacc tcttactctc tcacaatcag cagagtggag     300
gctgaagatg ctgccactta ttactgccag cagtggagtg gtaacccacg gacgttcggt     360
ggaggcacca agctggaaat caaa                                            384

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
agggccagct caagtgtaag ttacatgtac                                            30

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gccacatcca acctggcttc t                                                     21

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cagcagtgga gtggtaaccc acggacg                                               27

<210> SEQ ID NO 13
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met Tyr Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Asp Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Gly Asn Pro Arg Thr Phe Gly Gly Gly Thr Lys Leu Glu Ile Lys
        115                 120                 125

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ala Ser Ser Ser Val Ser Tyr Met Tyr
1               5                   10

<210> SEQ ID NO 15

-continued

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Thr Ser Asn Leu Ala Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Trp Ser Gly Asn Pro Arg Thr
1               5

<210> SEQ ID NO 17
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atgggatgga gctgggtctt tctcttcctc ctgtcagtga ctgcaggtgt ccactcccag      60
gttcacctgc agcagtctgg acctgaactg gtaaagcctg gggcttcagt gaagttgtcc    120
tgcaaggctt ctggctacac cttcacaaag tatgatataa actgggtgag gcagaggcct    180
gaacagggac ttgagtggat tggatggatt tttcctggag atggtagaac tgactacaat    240
gagaagttca gggtaaggc cacactgact acagacaaat cctccagcac agcctacatg      300
gaggtcagca ggctgacatc tgaggactct gctgtctatt tctgtgcaag atatggcccc    360
gctatggact actggggtca aggaacctca gtcaccgtcg cctca                    405

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aagtatgata taaac                                                      15

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19 tggattttc ctggagatgg tagaactgac tacaatgaga gttcaagggg t               51

<210> SEQ ID NO 20

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tatggccccg ctatggacta                                                     20

<210> SEQ ID NO 21
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Trp Ser Trp Val Phe Leu Phe Leu Leu Ser Val Thr Ala Gly
1               5                   10                  15

Val His Ser Gln Val His Leu Gln Gln Ser Gly Pro Glu Leu Val Lys
            20                  25                  30

Pro Gly Ala Ser Val Lys Leu Ser Cys Lys Ala Ser Gly Tyr Thr Phe
        35                  40                  45

Thr Lys Tyr Asp Ile Asn Trp Val Arg Gln Arg Pro Glu Gln Gly Leu
    50                  55                  60

Glu Trp Ile Gly Trp Ile Phe Pro Gly Asp Gly Arg Thr Asp Tyr Asn
65                  70                  75                  80

Glu Lys Phe Lys Gly Lys Ala Thr Leu Thr Thr Asp Lys Ser Ser Ser
                85                  90                  95

Thr Ala Tyr Met Glu Val Ser Arg Leu Thr Ser Glu Asp Ser Ala Val
            100                 105                 110

Tyr Phe Cys Ala Arg Tyr Gly Pro Ala Met Asp Tyr Trp Gly Gln Gly
        115                 120                 125

Thr Ser Val Thr Val Ala Ser
    130                 135

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Tyr Asp Ile Asn
1               5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Ile Phe Pro Gly Asp Gly Arg Thr Asp Tyr Asn Glu Lys Phe Lys
1               5                   10                  15

Gly
```

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Gly Pro Ala Met Asp Tyr
1               5

<210> SEQ ID NO 25
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atgaagttgc ctgttaggct gttggtgctg atgttctgga ttcctgcttc cagcagtgat      60
gttttgatga cccaaactcc actctccctg cctgtcagtc ttggagatca agcctccatc    120
tcttgcagat ctagtcagac cattgtacat agtaatggag acacctattt agactggttc    180
ctgcagaaac caggccagtc tccaaagctc ctgatctaca aagtttccaa ccgattttct    240
ggggtcccag acaggttcag tggcagtgga tcagggacag atttcacact caagatcagc    300
agagtggagg ctgaggatct gggagtttat tactgctttc aaggttcaca tgttccgtac    360
acgttcggag gggggaccaa gctggaaata aaa                                 393

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agatctagtc agaccattgt acatagtaat ggagacacct atttagac                  48

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aaagtttcca accgattttc t                                               21

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tttcaaggtt cacatgttcc gtacacg                                         27

```
<210> SEQ ID NO 29
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Thr Ile
        35                  40                  45

Val His Ser Asn Gly Asp Thr Tyr Leu Asp Trp Phe Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Tyr Thr Phe Gly Gly Gly Thr Lys Leu
        115                 120                 125

Glu Ile Lys
    130

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ser Ser Gln Thr Ile Val His Ser Asn Gly Asp Thr Tyr Leu Asp
1               5                   10                  15

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Val Ser Asn Arg Phe Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Gln Gly Ser His Val Pro Tyr Thr
1               5
```

-continued

```
<210> SEQ ID NO 33
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Leu Arg Ala Gln Gly Glu Ala Ser Val Gln Phe Gln Ala Leu Lys
1               5                   10                  15

Gly Gln Glu Phe Ala Pro Ser His Gln Gln Val Tyr Ala Pro Leu Arg
            20                  25                  30

Ala Asp Gly Asp Lys Pro Arg Ala His Leu Thr Val Val Arg Gln Thr
        35                  40                  45

Pro Thr Gln His Phe Lys Asn Gln Phe Pro Ala Leu His Trp Glu His
    50                  55                  60

Glu Leu Gly Leu Ala Phe Thr Lys Asn Arg Met Asn Tyr Thr Asn Lys
65                  70                  75                  80

Phe Leu Leu Ile Pro Glu Ser Gly Asp Tyr Phe Ile Tyr Ser Gln Val
                85                  90                  95

Thr Phe Arg Gly Met Thr Ser Glu Cys Ser Glu Ile Arg Gln Ala Gly
            100                 105                 110

Arg Pro Asn Lys Pro Asp Ser Ile Thr Val Val Ile Thr Lys Val Thr
        115                 120                 125

Asp Ser Tyr Pro Glu Pro Thr Gln Leu Leu Met Gly Thr Lys Ser Val
    130                 135                 140

Cys Glu Val Gly Ser Asn Trp Phe Gln Pro Ile Tyr Leu Gly Ala Met
145                 150                 155                 160

Phe Ser Leu Gln Glu Gly Asp Lys Leu Met Val Asn Val Ser Asp Ile
                165                 170                 175

Ser Leu Val Asp Tyr Thr Lys Glu Asp Lys Thr Phe Phe Gly Ala Phe
            180                 185                 190

Leu Leu

<210> SEQ ID NO 34
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
```

```
                   100                 105                 110
Gln Phe Pro Ala Leu His Trp Glu His Glu Leu Gly Leu Ala Phe Thr
                115                 120                 125

Lys Asn Arg Met Asn Tyr Thr Asn Lys Phe Leu Leu Ile Pro Glu Ser
        130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250
```

<210> SEQ ID NO 35
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Cys Asp Thr
            20                  25                  30

Tyr Met His Trp Val Lys Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Ala Thr Ile Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115
```

<210> SEQ ID NO 36
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Gln Val Gln Leu Val Gln Ser Gly Ala Glu Val Lys Lys Pro Gly Ala
1               5                   10                  15

Ser Val Lys Leu Ser Cys Lys Ala Ser Gly Phe Asp Ile Cys Asp Thr
```

```
                20                  25                  30
Tyr Met His Trp Val Arg Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Ala Thr Met Thr Thr Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
                100                 105                 110

Thr Val Ser Ser
        115

<210> SEQ ID NO 37
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Ala Glu Val Val Lys Pro Gly Ala
1               5                   10                  15

Ser Val Lys Leu Ser Cys Lys Ala Ser Gly Phe Asp Ile Cys Asp Thr
            20                  25                  30

Tyr Met His Trp Val Arg Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Thr Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
                100                 105                 110

Thr Val Ser Ser
        115

<210> SEQ ID NO 38
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Cys Asp Thr
            20                  25                  30

Tyr Met His Trp Val Lys Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Ala Thr Ile Thr Arg Asp Thr Ser Thr Ser Thr Ala Tyr
```

```
                65                  70                  75                  80
Leu Glu Leu Ser Ser Leu Arg Ser Glu Asp Thr Ala Val Tyr Tyr Cys
                    85                  90                  95

Ser Arg Ser Gly Gly Leu Pro Asp Val Trp Gly Gln Gly Thr Thr Val
                100                 105                 110

Thr Val Ser Ser
        115

<210> SEQ ID NO 39
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Cys Asp Thr
                20                  25                  30

Tyr Met His Trp Val Lys Gln Ala Pro Gly Gln Gly Leu Glu Trp Met
            35                  40                  45

Gly Arg Ile Asp Pro Ala Ser Gly His Thr Lys Tyr Asp Pro Lys Phe
        50                  55                  60

Gln Val Arg Ala Thr Met Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                    85                  90                  95

Ser Arg Ser Gly Gly Leu Pro Asp Val Trp Gly Gln Gly Thr Thr Val
                100                 105                 110

Thr Val Ser Ser
        115

<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Ile Val Leu Thr Gln Ser Pro Gly Thr Leu Ser Ala Ser Pro Gly
1               5                   10                  15

Glu Arg Ala Thr Met Ser Cys Arg Ala Ser Ser Ser Val Ser Tyr Met
                20                  25                  30

Tyr Trp Tyr Gln Gln Lys Pro Gly Gln Ala Pro Arg Pro Trp Ile Tyr
            35                  40                  45

Ala Thr Ser Asn Leu Ala Ser Gly Val Pro Asp Arg Phe Ser Gly Ser
        50                  55                  60

Gly Ser Gly Thr Asp Tyr Thr Leu Thr Ile Ser Arg Val Glu Pro Glu
65                  70                  75                  80

Asp Phe Ala Val Tyr Tyr Cys Gln Gln Trp Ser Gly Asn Pro Arg Thr
                    85                  90                  95

Phe Gly Gly Gly Thr Lys Leu Glu Ile Lys
                100                 105
```

```
<210> SEQ ID NO 41
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Ile Val Leu Thr Gln Ser Pro Gly Thr Leu Ser Leu Ser Pro Gly
1               5                   10                  15

Glu Arg Ala Thr Met Ser Cys Arg Ala Ser Ser Ser Val Ser Tyr Met
            20                  25                  30

Tyr Trp Tyr Gln Gln Lys Pro Gly Gln Ala Pro Arg Pro Trp Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Val Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 42
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Ile Val Leu Thr Gln Ser Pro Gly Thr Leu Ser Leu Ser Pro Gly
1               5                   10                  15

Glu Arg Val Thr Met Ser Cys Arg Ala Ser Ser Ser Val Ser Tyr Met
            20                  25                  30

Tyr Trp Tyr Gln Gln Lys Pro Gly Gln Ala Pro Arg Pro Trp Ile Tyr
        35                  40                  45

Ala Thr Ser Asn Leu Ala Ser Gly Val Pro Asp Arg Phe Ser Gly Ser
    50                  55                  60

Gly Ser Gly Thr Asp Phe Thr Leu Thr Ile Ser Arg Val Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Val Glu Ile Lys
            100                 105

<210> SEQ ID NO 43
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Ile Val Leu Thr Gln Ser Pro Gly Thr Leu Ser Ala Ser Pro Gly
1               5                   10                  15

Glu Arg Val Thr Leu Ser Cys Arg Ala Ser Ser Ser Val Ser Tyr Met
            20                  25                  30
```

Tyr Trp Tyr Gln Gln Lys Pro Gly Gln Ala Pro Arg Pro Trp Ile Tyr
            35                  40                  45

Ala Thr Ser Asn Leu Ala Ser Gly Val Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Ser Gly Asn Pro Arg Thr
                 85                  90                  95

Phe Gly Gly Gly Thr Lys Leu Glu Ile Lys
            100                 105

<210> SEQ ID NO 44
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Gly Thr Leu Ser Ala Ser Pro Gly
 1               5                  10                  15

Glu Arg Val Thr Met Ser Cys Arg Ala Ser Ser Ser Val Ser Tyr Met
                 20                  25                  30

Tyr Trp Tyr Gln Gln Lys Pro Gly Gln Ala Pro Arg Leu Leu Ile Tyr
            35                  40                  45

Ala Thr Ser Asn Leu Ala Ser Gly Val Pro Asp Arg Phe Ser Gly Ser
 50                  55                  60

Gly Ser Gly Thr Asp Phe Thr Leu Thr Ile Ser Arg Val Glu Pro Glu
 65                  70                  75                  80

Asp Phe Ala Val Tyr Tyr Cys Gln Gln Trp Ser Gly Asn Pro Arg Thr
                 85                  90                  95

Phe Gly Gly Gly Thr Lys Leu Glu Ile Lys
            100                 105

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 45

His His His His His His
 1               5

<210> SEQ ID NO 46
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Gly Trp Ser Trp Val Phe Leu Phe Leu Leu Ser Val Thr Ala Gly
 1               5                  10                  15

Val His Ser Gln Val His Leu Gln Gln Ser Gly Pro Glu Leu Val Lys
                 20                  25                  30

```
Pro Gly Ala Ser Val Lys Leu Ser Cys Lys Ala Ser Gly Tyr Thr Phe
            35                  40                  45

Thr Lys Tyr Asp Ile Asn Trp Val Arg Gln Arg Pro Glu Gln Gly Leu
 50                  55                  60

Glu Trp Ile Gly Trp Ile Phe Pro Gly Asp Gly Arg Thr Asp Tyr Asn
 65                  70                  75                  80

Glu Lys Phe Lys Gly Lys Ala Thr Leu Thr Thr Asp Lys Ser Ser Ser
                 85                  90                  95

Thr Ala Tyr Met Glu Val Ser Arg Leu Thr Ser Glu Asp Ser Ala Val
            100                 105                 110

Tyr Phe Cys Ala Arg Tyr Gly Pro Ala Met Asp Tyr Trp Gly Gln Gly
            115                 120                 125

Thr Ser Val Thr Val Ala Ser
        130                 135

<210> SEQ ID NO 47
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Lys Cys Ser Trp Val Ile Phe Phe Leu Met Ala Val Val Thr Gly
  1               5                  10                  15

Val Asn Ser Glu Val Gln Leu Gln Gln Ser Gly Ala Glu Leu Val Lys
             20                  25                  30

Pro Gly Ala Ser Val Lys Leu Ser Cys Thr Ala Ser Gly Phe Asp Ile
            35                  40                  45

Gln Asp Thr Tyr Met His Trp Val Lys Gln Arg Pro Glu Gln Gly Leu
 50                  55                  60

Glu Trp Ile Gly Arg Ile Asp Pro Ala Ser Gly His Thr Lys Tyr Asp
 65                  70                  75                  80

Pro Lys Phe Gln Val Lys Ala Thr Ile Thr Thr Asp Thr Ser Ser Asn
                 85                  90                  95

Thr Ala Tyr Leu Gln Leu Ser Ser Leu Thr Ser Glu Asp Thr Ala Val
            100                 105                 110

Tyr Tyr Cys Ser Arg Ser Gly Gly Leu Pro Asp Val Trp Gly Ala Gly
            115                 120                 125

Thr Thr Val Thr Val Ser Ser
        130                 135

<210> SEQ ID NO 48
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ser Ser Ser Asp Val Leu Met Thr Gln Thr Pro Leu Ser Leu Pro Val
  1               5                  10                  15

Ser Leu Gly Asp Gln Ala Ser Ile Ser Cys Arg Ser Ser Gln Thr Ile
             20                  25                  30

Val His Ser Asn Gly Asp Thr Tyr Leu Asp Trp Phe Leu Gln Lys Pro
            35                  40                  45
```

```
Gly Gln Ser Pro Lys Leu Leu Ile Tyr Lys Val Ser Asn Arg Phe Ser
    50                  55                  60

Gly Val Pro Asp Arg Phe Ser Gly Ser Gly Ser Gly Thr Asp Phe Thr
65                  70                  75                  80

Leu Lys Ile Ser Arg Val Glu Ala Glu Asp Leu Gly Val Tyr Tyr Cys
                85                  90                  95

Phe Gln Gly Ser His Val Pro Tyr Thr Phe Gly Gly Gly Thr Lys Leu
                100                 105                 110

Glu Ile Lys
        115

<210> SEQ ID NO 49
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ser Arg Gly Gln Ile Val Leu Ser Gln Ser Pro Ala Ile Leu Ser Ala
1               5                   10                  15

Ser Pro Gly Glu Lys Val Thr Met Thr Cys Arg Ala Ser Ser Ser Val
                20                  25                  30

Ser Tyr Met Tyr Trp Tyr Gln Gln Lys Pro Gly Ser Ser Pro Lys Pro
            35                  40                  45

Trp Ile Tyr Ala Thr Ser Asn Leu Ala Ser Gly Val Pro Asp Arg Phe
        50                  55                  60

Ser Gly Ser Gly Ser Gly Thr Ser Tyr Ser Leu Thr Ile Ser Arg Val
65                  70                  75                  80

Glu Ala Glu Asp Ala Ala Thr Tyr Tyr Cys Gln Gln Trp Ser Gly Asn
                85                  90                  95

Pro Arg Thr Phe Gly Gly Gly Thr Lys Leu Glu Ile Lys
                100                 105
```